(12) United States Patent
Nakade

(10) Patent No.: US 10,085,617 B2
(45) Date of Patent: Oct. 2, 2018

(54) ENDOSCOPIC CHANNEL SWITCHING DEVICE, ENDOSCOPE, AND MANUFACTURING METHOD OF ENDOSCOPIC CHANNEL SWITCHING DEVICE

(71) Applicant: OLYMPUS CORPORATION, Shibuya-ku, Tokyo (JP)

(72) Inventor: Toshihiko Nakade, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 258 days.

(21) Appl. No.: 14/726,840

(22) Filed: Jun. 1, 2015

(65) Prior Publication Data
US 2015/0257634 A1 Sep. 17, 2015

Related U.S. Application Data

(63) Continuation of application No. PCT/JP2014/055237, filed on Mar. 3, 2014.

(30) Foreign Application Priority Data

Apr. 18, 2013 (JP) ................................ 2013-087269

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/005* (2013.01); *A61B 1/015* (2013.01);
(Continued)

(58) Field of Classification Search
CPC ............ A61B 1/00066; A61B 1/00068; A61B 1/00121; A61B 1/00128; A61B 1/00112; A61B 1/015; A61B 1/12
(Continued)

(56) References Cited

U.S. PATENT DOCUMENTS

| 4,562,830 A * | 1/1986 | Yabe .................. A61B 1/00068 600/155 |
| 2012/0088975 A1* | 4/2012 | Morimoto .............. A61B 1/015 600/159 |

FOREIGN PATENT DOCUMENTS

| JP | 59011828 A | 1/1984 | |
| JP | 08215137 A * | 8/1996 | ............. A61B 1/015 |

(Continued)

OTHER PUBLICATIONS

Chinese Office Action (and English translation thereof) dated Mar. 4, 2016, issued in counterpart Chinese Application No. 201480003494.7.

(Continued)

*Primary Examiner* — Ryan Henderson
(74) *Attorney, Agent, or Firm* — Holtz, Holtz & Volek PC

(57) ABSTRACT

A blocked end portion of a cylinder is provided closer to a distal end side in a direction of insertion of the piston into the cylinder than a minimum diameter portion. The blocked end portion includes a minimum diameter uniform portion which has the same inside diameter as the minimum diameter portion and a partial diameter increased portion which has an inside diameter that is increased as compared to the inside diameter of the minimum diameter portion.

10 Claims, 11 Drawing Sheets

(51) Int. Cl.
*A61B 1/12* (2006.01)
*A61B 17/34* (2006.01)
*A61M 39/22* (2006.01)
*A61B 1/005* (2006.01)
*B23P 15/00* (2006.01)

(52) U.S. Cl.
CPC ............... *A61B 1/12* (2013.01); *A61M 39/22* (2013.01); *A61M 39/223* (2013.01); *B23P 15/001* (2013.01); *A61B 1/0011* (2013.01); *A61B 1/00119* (2013.01); *A61B 1/00128* (2013.01); *A61B 17/3498* (2013.01); *A61M 2039/224* (2013.01); *Y10T 29/49405* (2015.01)

(58) Field of Classification Search
USPC ................. 600/133, 156–159; 604/121, 135, 604/218–238
See application file for complete search history.

(56) References Cited

FOREIGN PATENT DOCUMENTS

| | | |
|---|---|---|
| JP | 09122069 A | 5/1997 |
| JP | 2003180623 A | 7/2003 |

OTHER PUBLICATIONS

International Preliminary Report on Patentability (IPRP) including Written Opinion (in English) dated Oct. 29, 2015, issued in parent International Application No. PCT/JP2014/055237.
International Search Report (ISR) dated Mar. 25, 2014 issued in International Application No. PCT/JP2014/055237.
Chinese Office Action (and English translation thereof) dated Mar. 4, 2016, issued in counterpart Chinese Application No. 20148003494.7.

* cited by examiner

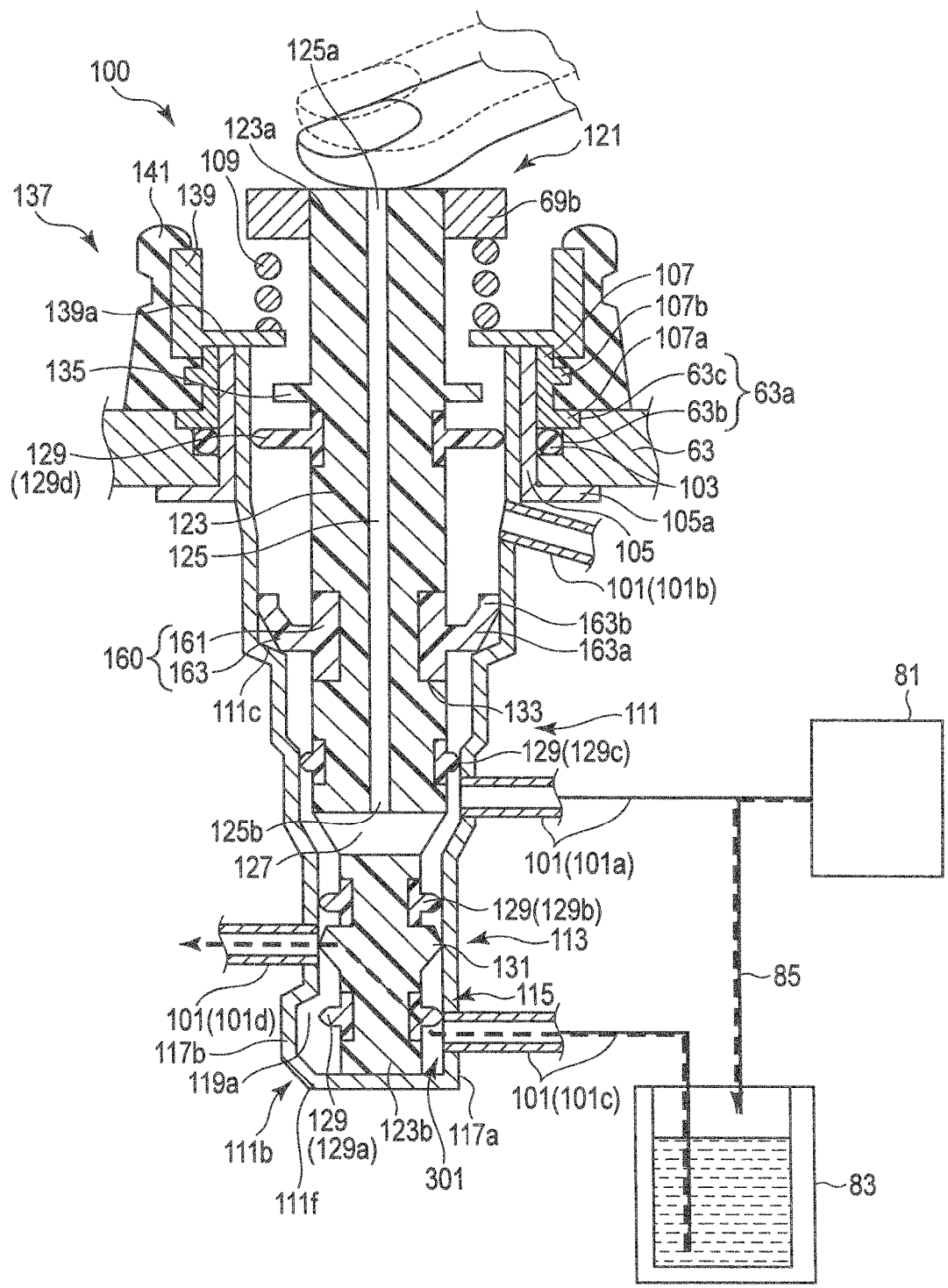
F I G. 4C

ENDOSCOPIC CHANNEL SWITCHING DEVICE, ENDOSCOPE, AND MANUFACTURING METHOD OF ENDOSCOPIC CHANNEL SWITCHING DEVICE

CROSS-REFERENCE TO RELATED APPLICATIONS

This application is a Continuation application of PCT Application No. PCT/JP2014/055237, filed Mar. 3, 2014 and based upon and claiming the benefit of priority from prior Japanese Patent Application No. 2013-087269, filed Apr. 18, 2013, the entire contents of all of which are incorporated herein by reference.

BACKGROUND OF THE INVENTION

1. Field of the Invention

The present invention relates to an endoscopic channel switching device which switches the communication states of channel portions in an endoscope, an endoscope, and a manufacturing method of an endoscopic channel switching device.

2. Description of the Related Art

Generally, an endoscope has an observation window for observation in a body cavity. The field of view of the observation window narrows when, for example, body fluid sticks to the observation window. Thus, the endoscope requires the supply of at least one of air and water to the observation window to ensure the field of view. The endoscope has a switching device for switching from one of the air supply and water supply to the other. The switching device has a piston and a cylinder. The piston moves relative to the cylinder, so that one of the air supply and water supply is switched to the other.

Such endoscopes have been disclosed in, for example, Jpn. Pat. Appln. KOKAI Publication No. 9-122069 and Jpn. Pat. Appln. KOKAI Publication No. 59-11828. In Jpn. Pat. Appln. KOKAI Publication No. 9-122069 and Jpn. Pat. Appln. KOKAI Publication No. 59-11828, a piston moves relative to a cylinder, so that one of air supply and water supply is switched to the other.

In Jpn. Pat. Appln. KOKAI Publication No. 9-122069 and Jpn. Pat. Appln. KOKAI Publication No. 59-11828, the cylinder has a diametrically increased portion which is provided in the lower part of the cylinder and which has an inside diameter larger than the minimum inside diameter of the cylinder. That is, the inside diameter of the lower part of the cylinder is larger than the minimum inside diameter of the cylinder. In other words, the whole lower part of the cylinder is bulging in the diametrical direction of the cylinder.

In the diametrically increased portion, a hole portion is provided in the circumferential surface of the cylinder. An end portion of a channel portion is provided inside the cylinder through the hole portion. This channel portion is coupled to the cylinder, for example, by welding. Since the diametrically increased portion is provided, a coupling part between the channel portion and the cylinder is provided outside the thinnest portion of the cylinder in the diametrical direction of the cylinder.

The end portion of the channel portion is inserted in the cylinder. Thus, in this end portion, a part inserted in the cylinder is cut and removed by a tool. The coupling part has an uneven surface formed by welding. This uneven surface is also cut and removed by the tool as a finishing process.

BRIEF SUMMARY OF THE INVENTION

An aspect of an endoscopic channel switching device including a cylinder to which channel portions are connected; a piston removably fitted into the cylinder, the communication states of the channel portions being switched in accordance with the movement of the piston relative to the cylinder; and a blocked end portion of the cylinder provided closer to a distal end side in a direction of insertion of the piston into the cylinder than a minimum diameter portion of the cylinder in a axial direction of the cylinder, the blocked end portion including a minimum diameter uniform portion which is provided in one part of the blocked end portion, which has the same inside diameter as the minimum diameter portion and which is provided flush with one part of the minimum diameter portion in the axial direction of the cylinder, the channel portion being connected to the minimum diameter uniform portion, and a partial diameter increased portion which is provided in the other part of the blocked end portion and which has an inside diameter that is increased as compared to the inside diameter of the minimum diameter portion, the partial diameter increased portion bulging out to the minimum diameter portion in the diametrical direction of the cylinder, the partial diameter increased portion continuing to the minimum diameter uniform portion in a circumferential direction of the cylinder, the partial diameter increased portion being provided flush with the minimum diameter uniform portion in a plane that intersects at right angles with the axial direction of the cylinder.

An aspect of an endoscope including an insertion portion to be inserted into a lumen; a channel portion which is inserted through the insertion portion; and the endoscopic channel switching device according to above.

An aspect of a manufacturing method of an endoscopic channel switching device including a cylinder to which channel portions are connected, and a piston removably fitted into the cylinder, the endoscopic channel switching device switching the communication states of the channel portions in accordance with the movement of the piston relative to the cylinder, including the steps of: subjecting a thin plate to a deep-draw stepped pressing process so that the tapered cylinder having an opening portion which functions as an insertion opening portion to fit the piston through the cylinder and a bottom portion is formed; forming, by bulging, a minimum diameter uniform portion and a partial diameter increased portion at a blocked end portion of the cylinder provided closer to a distal end side in a direction of insertion of the piston into the cylinder than a minimum diameter portion of the cylinder in a axial direction of the cylinder, the minimum diameter uniform portion being provided in one part of the blocked end portion, having the same inside diameter as the minimum diameter portion, and being provided flush with one part of the minimum diameter portion in the axial direction of the cylinder, the channel portion being connected to the minimum diameter uniform portion, the partial diameter increased portion being provided in the other part of the blocked end portion and having an inside diameter that is increased as compared to the inside diameter of the minimum diameter portion, the partial diameter increased portion bulging out to the minimum diameter portion in the diametrical direction of the cylinder, the partial diameter increased portion continuing to the minimum diameter uniform portion in a circumferential direction of the cylinder, the partial diameter increased portion being provided flush with the minimum diameter uniform portion in a plane that intersects at right angles with the axial direction of the cylinder; forming, by a pressing process, a side surface hole portion in a circumferential surface of the cylinder in the minimum diameter uniform portion; and joining the channel portion to the side surface hole portion, and coupling the channel portions to the cylinder.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4C is a diagram showing the endoscopic channel switching device in a water supplied state.

DETAILED DESCRIPTION OF THE INVENTION

Hereinafter, one embodiment of the present invention will be described in detail with reference to the drawings.

One Embodiment

[Configuration]

One embodiment is described with reference to FIG. 1, FIG. 2A, FIG. 2B, FIG. 2C, FIG. 2D, FIG. 2E, FIG. 3A, FIG. 3B, FIG. 3C, FIG. 3D, FIG. 4A, FIG. 4B, and FIG. 4C. In some of the drawings, some components are not shown for clarity of diagrammatic representation.

[Endoscope 1]

Figure 1:
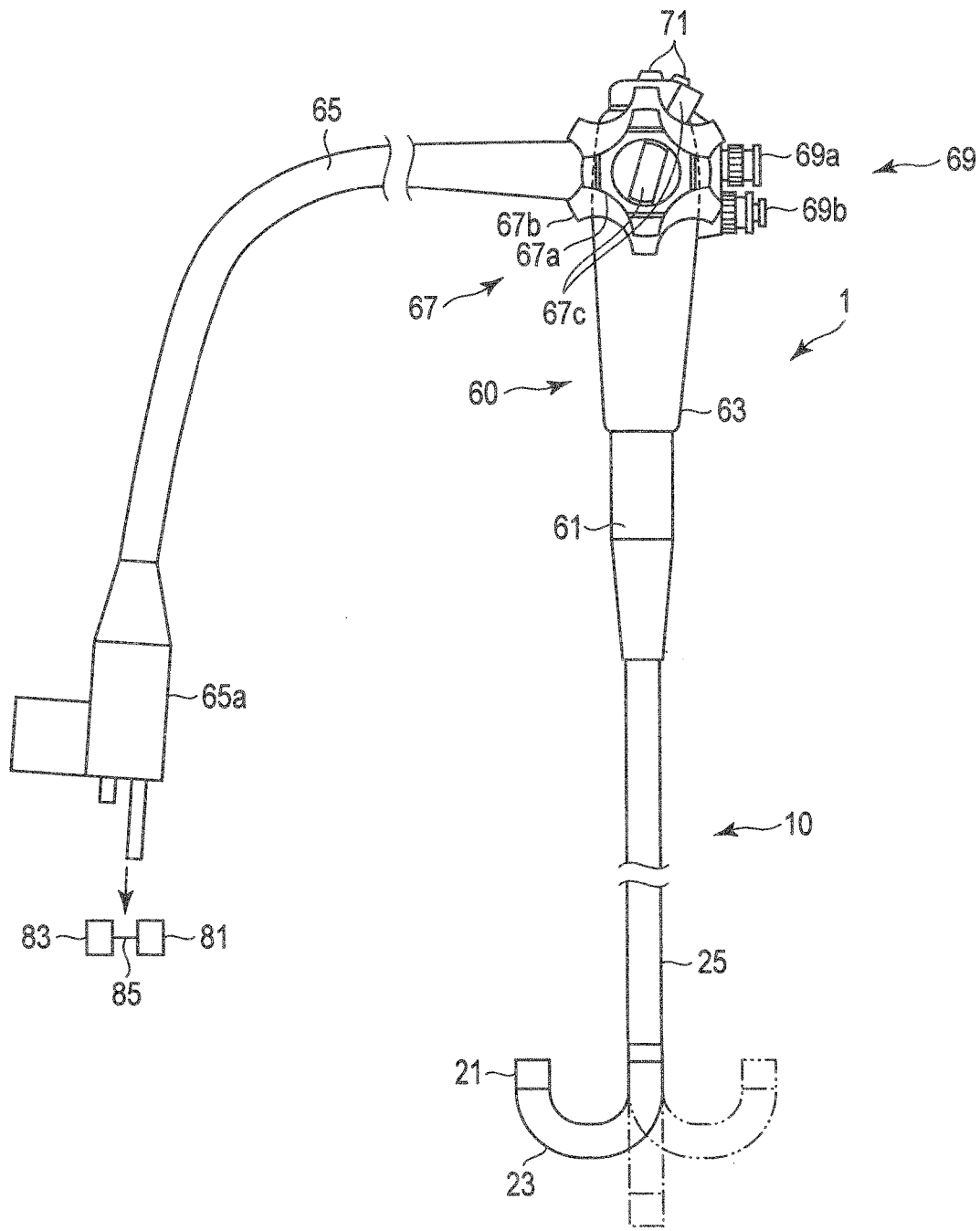
FIG. 1 is a schematic diagram of an endoscope according to the present invention.

As shown in FIG. 1, an endoscope 1 has an elongated insertion portion 10 to be inserted into, for example, a body cavity of a patient, and an operation portion 60 which is coupled to the proximal end portion of the insertion portion 10 and which operates the endoscope 1.

[Insertion Portion 10]

The insertion portion 10 has a distal hard portion 21, a bending portion 23, and a flexible tubular portion 25 from a distal end portion side of the insertion portion 10 to a proximal end portion side of the insertion portion 10. A proximal end portion of the distal hard portion 21 is coupled to a distal end portion of the bending portion 23. A proximal end portion of the bending portion 23 is coupled to a distal end portion of the flexible tubular portion 25.

The distal hard portion 21 functions as a distal end portion of the insertion portion 10. The distal hard portion 21 is hard and unbendable.

The bending portion 23 is bent in a desired direction, for example, in an upward, downward, leftward, or rightward direction by an operation of a bending operation portion 67 described later. When the bending portion 23 is bent, a position and direction of the distal hard portion 21 change. Accordingly, an observation target is illuminated by illumination light, and the observation target is caught in an observation field.

The flexible tubular portion 25 has desired flexibility to be bent by an appropriate external force. The flexible tubular portion 25 is a tubular member extending from a later-described body portion 61 in the operation portion 60.

[Operation Portion 60]

The operation portion 60 has the body portion 61 from which the flexible tubular portion 25 extends, a grip portion 63 which is coupled to a proximal end portion of the body portion 61 and which is held by an operator who operates the endoscope 1, and a universal cord 65 connected to the grip portion 63.

[Grip Portion 63]

The grip portion 63 has the bending operation portion 67 which is operated to bend the bending portion 23. The bending operation portion 67 has a vertical bending operation knob 67a which is operated to vertically bend the bending portion 23, a horizontal bending operation knob 67b which is operated to horizontally bend the bending portion 23, and a fixing knob 67c which fixes the position of the bent bending portion 23.

The grip portion 63 also has a button portion 69. The button portion 69 has a suction button 69a and an air/water supply button 69b. The suction button 69a and the air/water supply button 69b are operated by the hand of the operator when the grip portion 63 is held by the operator. The air/water supply button 69b is operated when the fluid is supplied from an air/water supply channel (not shown in the drawings) to secure an observation field of an imaging unit (not shown in the drawings) in the distal hard portion 21. The fluid includes a liquid such as water, and gases such as air. The air and water are supplied to an observation window in the imaging unit provided in a distal face of the distal hard portion 21.

The grip portion 63 has various remote switches 71 for endoscopic photography.

[Universal Cord 65]

The universal cord 65 has a connection portion 65a to be connected to a video processor (not shown in the drawings), a light source device (not shown in the drawings), an air supply device 81, and a water supply device 83. The video processor, the light source device, the air supply device 81, and the water supply device 83 are provided, for example, outside the endoscope 1. The air supply device 81 has, for example, an air supply pump for supplying the air. The air supply device 81 is connected to the water supply device 83 by a channel portion 85. The water supply device 83 has a filling tank to be filled with a liquid to be supplied.

[Endoscopic Channel Switching Device (Hereinafter, Channel Switching Device 100)]

Next, a channel switching device 100 according to the present embodiment is described with reference to FIG. 2A, FIG. 2B, FIG. 2C, FIG. 2D, and FIG. 2E. Hereinafter, the upper part indicates, for example, the outside of the grip portion 63, and indicates the side of the air/water supply button 69b in an axial direction of the channel switching device 100. The lower part indicates, for example, the inside of the grip portion 63, and indicates the side of the other end portion 111b of a cylinder 111 in the axial direction of the channel switching device 100.

Figure 2A:
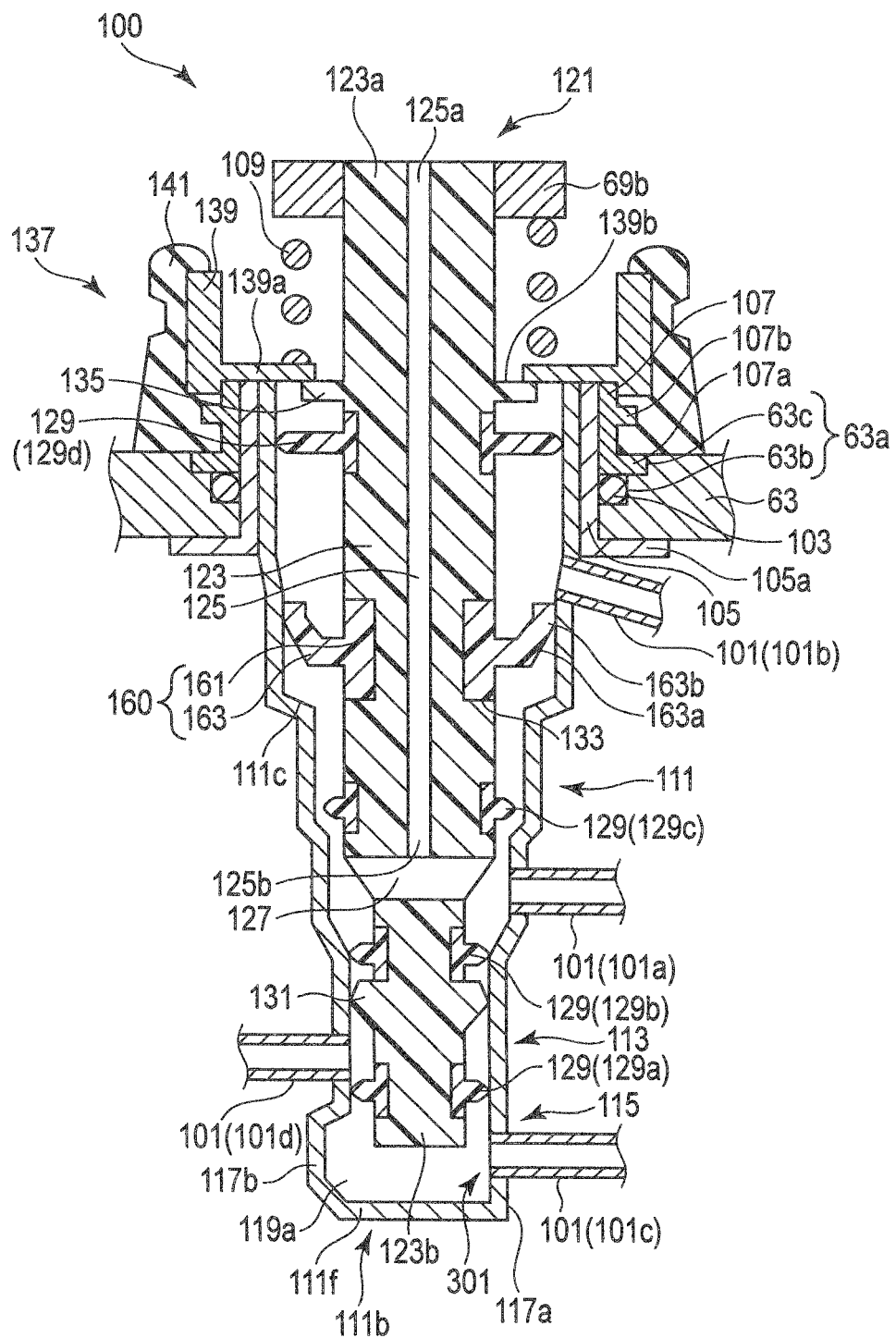
FIG. 2A is a diagram showing an endoscopic channel switching device according to one embodiment.
Figure 2B:
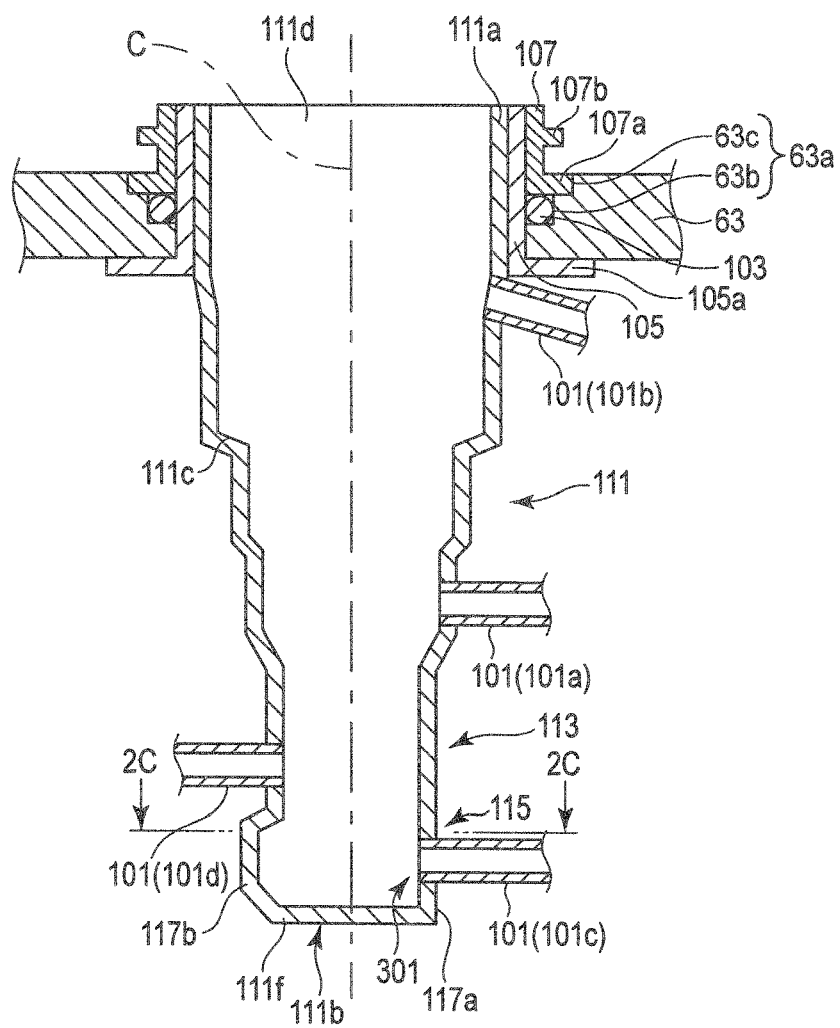
FIG. 2B is a diagram showing a cylinder.

As shown in FIG. 2A, FIG. 4A, FIG. 4B, and FIG. 4C, the channel switching device 100 has the above-mentioned air/water supply button 69b, which is an operation portion to be operated when the above-mentioned air/water supply button 69b switches one of air supply and water supply to the other, and when the air/water supply button 69b allows the air supply or the water supply as described above. As shown in FIG. 2A, FIG. 2B, and FIG. 2E, the channel switching device 100 has the cylinder 111 to which channel portions 101 are connected, and a piston 121 which is connected to the air/water supply button 69b and which is removably fitted into the cylinder 111. The channel switching device 100 switches the communication states of the channel portions 101 in accordance with the movement of the piston 121 relative to the cylinder 111.

[Cylinder 111]

The cylinder 111 is described with reference to FIG. 2A and FIG. 2B.

The cylinder 111 has, for example, an essentially circular cylindrical shape with a central axis C. The cylinder 111 is made of a metallic material such as stainless steel. The cylinder 111 has one end portion 111a which is opened, and the other end portion 111b which is closed. The cylinder 111 is tapered from the side of the one end portion 111a (an opening portion 111d) toward the side of the other end portion 111b (a bottom portion 111f) along a axial direction of the cylinder 111 so that the cylinder 111 is stepped. The cylinder 111 is tapered so that the cylinder 111 has an abutment surface 111c which is formed on the inner circumferential surface of the cylinder 111 and which is diagonal to the axial direction of the cylinder 111. The abutment surface 111c is provided between an air supply inlet channel portion 101a and an air supply outlet channel portion 101b, which will be described later, in the axial direction of the cylinder 111. The inclination angle of the abutment surface 111c is not particularly limited. This cylinder 111 is molded by, for example, a deep-draw stepped pressing process. Specifically, a thin plate is subjected to the deep-draw stepped pressing process so that the opening portion 111d, the bottom portion 111f, and the abutment surface 111c may be provided, whereby the tapered cylinder 111 having the opening portion 111d, the bottom portion 111f, and the abutment surface 111c is formed. The cylinder 111 does not need to be exclusively molded by this method, and may be molded by, for example, a cutting process. The molding method of the cylinder 111 according to the present embodiment may also be used for a suction channel switching device.

The one end portion 111a has the opening portion 111d which functions as an insertion opening portion to fit the piston 121 through the cylinder 111. The other end portion 111b has the bottom portion 111f which faces the opening portion 111d in the axial direction of the cylinder 111 and which is smaller than the opening portion 111d. The opening portion 111d and the bottom portion 111f are at the greatest distance from each other in the axial direction of the cylinder 111. The bottom portion 111f is integral with a circumferential surface of the cylinder 111 as a result of the above-mentioned processing.

[Minimum Diameter Portion 113]

As shown in FIG. 2A and FIG. 2B, the cylinder 111 has a minimum diameter portion 113 provided in the lower part (on the side of the other end portion 111b) of the cylinder 111 in the axial direction of the cylinder 111. The minimum diameter portion 113 is provided higher than the bottom portion 111f. This minimum diameter portion 113 includes the circumferential surface of the cylinder 111, and a space portion surrounded by this circumferential surface.

As shown in FIG. 2A and FIG. 2B, the minimum diameter portion 113 indicates the portion in which the diameter of the cylinder 111 is the smallest. Specifically, the inside diameter of the cylinder 111 in the minimum diameter portion 113 is the smallest of the inside diameter of the cylinder 111. The inside diameter of the cylinder 111 in the minimum diameter portion 113 is the same as the outside diameters of sealing members 129a and 129b described later. The inner circumferential surface of the cylinder 111 in the minimum diameter portion 113 is in close contact with the sealing members 129a and 129b. The sealing members 129a and 129b slide on this inner circumferential surface in the axial direction of the cylinder 111.

In the minimum diameter portion 113, the cylinder 111 is connected to a water supply outlet channel portion 101d. The minimum diameter portion 113 has a rotationally symmetric shape around the central axis C, for example, a circular cylindrical shape.

[Blocked End Portion 115]

As shown in FIG. 2A, FIG. 2B, FIG. 2C, and FIG. 2D, the cylinder 111 has a blocked end portion 115 provided closer to the distal end side in the direction of insertion of the piston 121 into the cylinder 111 than the minimum diameter portion 113 in the axial direction of the cylinder 111 (the direction along the central axis C). In other words, the blocked end portion 115 is provided in the lower part of the cylinder 111 than the minimum diameter portion 113 in the axial direction of the cylinder 111. The blocked end portion 115 is provided between the bottom portion 111f and the minimum diameter portion 113 to be adjacent to the bottom portion 111f and the minimum diameter portion 113 in the axial direction of the cylinder 111. The blocked end portion 115 is provided apart from the opening portion 111d in the axial direction of the cylinder 111. The blocked end portion 115 has only to be isolated from the opening portion 111d and provided lower than the minimum diameter portion 113, and is preferably at the greatest distance from the opening portion 111d. The blocked end portion 115 is in communication with the minimum diameter portion 113 in the axial direction of the cylinder 111. This blocked end portion 115 includes the inner circumferential surface of the cylinder 111, and a space portion surrounded by this circumferential surface.

As shown in FIG. 2A, FIG. 2B, FIG. 2C, and FIG. 2D, the blocked end portion 115 has a minimum diameter uniform portion 117a which is provided in one part of the blocked end portion 115 and which has the same inside diameter as the minimum diameter portion 113, and a partial diameter increased portion 117b which is provided in the other part of the blocked end portion 115 and which has an inside diameter that is increased as compared to the inside diameter of the minimum diameter portion 113. That is, one part of the blocked end portion 115 corresponding to the minimum diameter uniform portion 117a has the same inside diameter as the minimum diameter portion 113, and the other part of the blocked end portion 115 corresponding to the partial diameter increased portion 117b has an inside diameter larger than that of the minimum diameter portion 113. In other words, the blocked end portion 115 is not rotationally symmetric with respect to the central axis C, and is locally increased in diameter compared to the minimum diameter portion 113.

This blocked end portion 115 is not formed separately from the minimum diameter portion 113 and the cylinder 111. One part of the circumferential surface of the cylinder 111, located in the lowermost part of the minimum diameter portion 113, is bulged to form the partial diameter increased portion 117b. The unbulged other part of the circumferential surface of the cylinder 111, located in the lowermost part of the minimum diameter portion 113, functions as the minimum diameter uniform portion 117a.

Figure 2C:
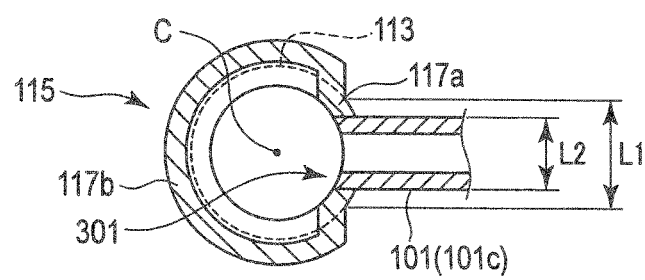
FIG. 2C is a diagram showing a blocked end portion along the line 2C-2C shown in FIG. 2B.
Figure 2D:
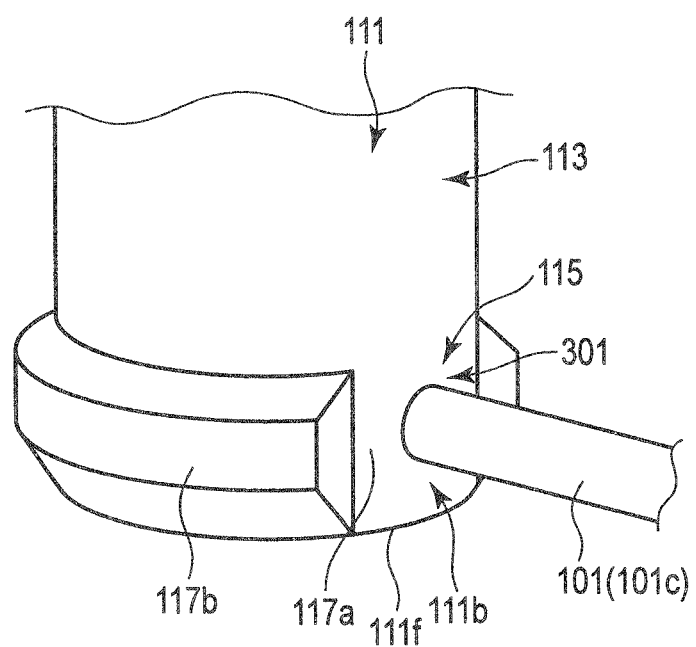
FIG. 2D is a perspective view of a part around the blocked end portion.
Figure 2E:
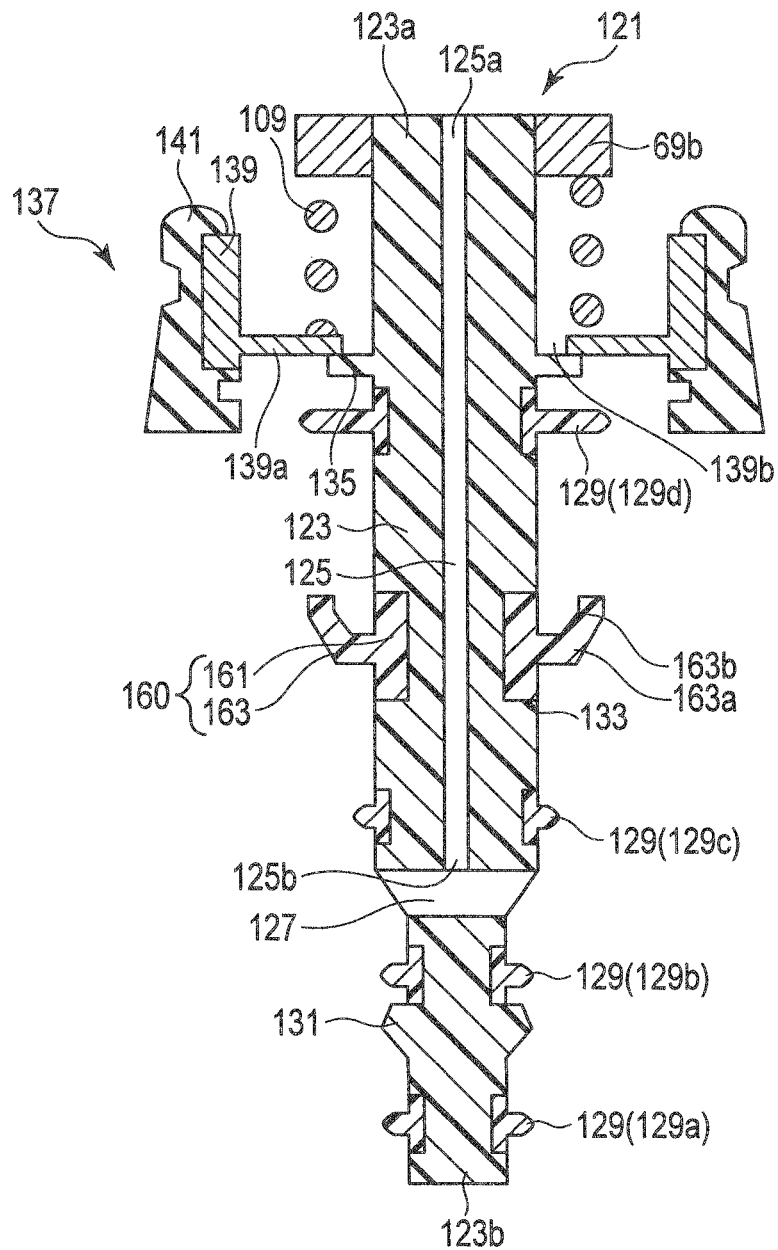
FIG. 2E is a diagram showing a piston.

Thus, as shown in FIG. 2C and FIG. 2D, the minimum diameter uniform portion 117a and the partial diameter increased portion 117b adjacently continue to each other in a circumferential direction of the cylinder 111. The minimum diameter uniform portion 117a and the partial diameter increased portion 117b are provided flush with each other in a plane that intersects at right angles with the axial direction of the central axis C of the cylinder 111. That is, the minimum diameter uniform portion 117a and the partial diameter increased portion 117b are shared in the same plane.

The minimum diameter uniform portion 117a includes the circumferential surface of the cylinder 111, and a space portion surrounded by this circumferential surface.

The partial diameter increased portion 117b includes the circumferential surface of the cylinder 111, and a space portion surrounded by this circumferential surface.

A central position of the minimum diameter uniform portion 117a and a central position of the partial diameter increased portion 117b are the same each other, located on the central axis C, and correspond to the central position of the piston 121.

[Minimum Diameter Uniform Portion 117a]

As shown in FIG. 2A, FIG. 2B, and FIG. 2D, the minimum diameter uniform portion 117a is provided flush with one part of the minimum diameter portion 113 in the axial direction of the central axis C of the cylinder 111. Thus, the minimum diameter uniform portion 117a is neither bulged out nor pulled in relative to the minimum diameter portion 113 in a diametrical direction of the cylinder 111. Therefore, the inner circumferential surface of the cylinder 111 in the minimum diameter uniform portion 117a is stepless and smooth in the axial direction of the cylinder 111 to the inner circumferential surface of the cylinder 111 in the minimum diameter portion 113. That is, the minimum diameter uniform portion 117a follows one part of the minimum diameter portion 113.

As shown in FIG. 2A, FIG. 4A, FIG. 4B, and FIG. 4C, the inner circumferential surface of the cylinder 111 in the minimum diameter uniform portion 117a is always in close contact with the sealing member 129a so that the sealing member 129a may slide on the inner circumferential surface of the cylinder 111 in the axial direction of the central axis C of the cylinder 111 in accordance with the movement of the piston 121 for channel switching.

As shown in FIG. 2A, FIG. 2B, FIG. 2C, and FIG. 2D, the circumferential surface of the cylinder 111 in the minimum diameter uniform portion 117a is connected to a water supply inlet channel portion 101c. Thus, a coupling part 301 between the water supply inlet channel portion 101c and the cylinder 111 is not provided outside the minimum diameter portion 113 in the diametrical direction of the cylinder 111, and is provided flush with the minimum diameter portion 113 in the axial direction of the cylinder 111. Specifically, the coupling part 301 is provided in the minimum diameter uniform portion 117a, so that the coupling part 301 on the outer circumferential side of the cylinder 111 is provided flush with the outer circumferential surface of the cylinder 111 in the minimum diameter portion 113 in the axial direction of the cylinder 111, and the coupling part 301 on the inner circumferential side of the cylinder 111 is provided flush with the inner circumferential surface of the cylinder 111 in the minimum diameter portion 113 in the axial direction of the cylinder 111.

The circumferential surface of the cylinder 111 in the minimum diameter uniform portion 117a is, for example, arc-shaped. As shown in FIG. 2C, a length L1 of a chord of the minimum diameter uniform portion 117a is longer than a diameter L2 of the air supply inlet channel portion 101a. It is also possible that L1=L2, and it is only necessary that L1≥L2.

[Partial Diameter Increased Portion 117b]

As shown in FIG. 2A, FIG. 2B, FIG. 2C, and FIG. 2D, the partial diameter increased portion 117b bulges out to the minimum diameter portion 113 in the diametrical direction of the cylinder 111. Thus, as shown in FIG. 2A, FIG. 4A, FIG. 4B, and FIG. 4C, the inner circumferential surface of the cylinder 111 in the partial diameter increased portion 117b is not in close contact with the sealing member 129a. As shown in FIG. 2A, FIG. 4A, FIG. 4B, and FIG. 4C, this inner circumferential surface is out of close contact and out of abutment with the sealing member 129a so that a clearance portion 119a as a flow portion may be formed between the inner circumferential surface and the sealing member 129a in the diametrical direction of the cylinder 111. That is, the inner circumferential surface of the cylinder 111 in the partial diameter increased portion 117b is not in close contact with and not in abutment with the sealing member 129a.

The partial diameter increased portion 117b is formed by, for example, bulging after a thin plate is subjected to the deep-draw stepped process and the tapered cylinder 111 having the bottom portion 111f is formed.

The circumferential surface of the cylinder 111 in the partial diameter increased portion 117b is, for example, arc-shaped, more specifically, is essentially C-shaped.

[Channel Portions 101]

The cylinder 111 has hole portions to communicate with the channel portions 101. One channel portion 101 is joined to one hole portion.

As shown in FIG. 2B, the channel portions 101 have, for example, the air supply inlet channel portion 101a, the air supply outlet channel portion 101b, the water supply inlet channel portion 101c, and the water supply outlet channel portion 101d. As shown in FIG. 2B, the air supply outlet channel portion 101b, the air supply inlet channel portion 101a, the water supply outlet channel portion 101d, and the water supply inlet channel portion 101c are provided in order from the one end portion 111a to the other end portion 111b.

[Air Supply Inlet Channel Portion 101a]

The air supply inlet channel portion 101a is provided from the inside of the grip portion 63 to the inside of the universal cord 65. The air supply inlet channel portion 101a is provided inside the universal cord 65 along the universal cord 65. The air supply inlet channel portion 101a is connected to the connection portion 65a via the universal cord 65. When the connection portion 65a is connected to the air supply device 81, the air supply inlet channel portion 101a is connected to the air supply device 81, and the gas is supplied to the air supply inlet channel portion 101a from the air supply device 81. The air supply inlet channel portion 101a functions as an air supply channel portion.

[Air Supply Outlet Channel Portion 101b]

The air supply outlet channel portion 101b is provided inside the operation portion 60 and inside the insertion portion 10 along the operation portion 60 and the insertion portion 10. The air supply outlet channel portion 101b is in communication with an air/water supply nozzle (not shown in the drawings) provided in the distal hard portion 21. The air supply outlet channel portion 101b supplies the air/water supply nozzle with the gas supplied from the air supply inlet channel portion 101a.

[Water Supply Inlet Channel Portion 101c]

The water supply inlet channel portion 101c is provided from the inside of the grip portion 63 to the inside of the universal cord 65. The water supply inlet channel portion 101c is provided inside the universal cord 65 along the universal cord 65. The water supply inlet channel portion 101c is connected to the connection portion 65a via the universal cord 65. When the connection portion 65a is connected to the water supply device 83, the water supply inlet channel portion 101c is connected to the water supply device 83, and a liquid is supplied to the water supply inlet channel portion 101c from the water supply device 83. The water supply inlet channel portion 101c functions as a water supply channel portion.

[Water Supply Outlet Channel Portion 101d]

The water supply outlet channel portion 101d is provided inside the operation portion 60 and inside the insertion portion 10 along the operation portion 60 and the insertion portion 10. The water supply outlet channel portion 101d is in communication with an air/water supply nozzle (not shown in the drawings) provided in the distal hard portion 21. The water supply outlet channel portion 101d supplies the air/water supply nozzle with the liquid supplied from the water supply inlet channel portion 101c.

[Location of Cylinder 111]

As shown in FIG. 2B, the cylinder 111 is removably inserted into a hole portion 63a provided in the grip portion 63, and fixed to the grip portion 63. An inside diameter of the hole portion 63a is larger than an outside diameter of the cylinder 111. The hole portion 63a has a lower annular groove portion 63b in which an O-ring 103 is provided, and an upper annular groove portion 63c which is provided higher than the lower annular groove portion 63b and into which a lower flange portion 107a of a later-described mouthpiece 107 fits. The lower annular groove portion 63b is smaller than the upper annular groove portion 63c, and is provided coaxially with the upper annular groove portion 63c. The lower annular groove portion 63b continues to the upper annular groove portion 63c in the thickness direction of the grip portion 63.

As shown in FIG. 2B, the cylinder 111 is fixed to the grip portion 63 by a holding member 105 and the mouthpiece 107 via the hole portion 63a.

The holding member 105 is ring-shaped, and the inner circumferential surface of the holding member 105 is joined to the outer circumferential surface on the side of the one end portion 111a. The holding member 105 has a flange portion 105a formed outward in a diametrical direction of the holding member 105. The flange portion 105a is provided inside the grip portion 63. The hole portion 63a has a thread groove (not shown in the drawings) provided in an inner circumferential surface of the hole portion 63a, and the holding member 105 has a thread groove (not shown in the drawings) provided in an outer circumferential surface of the holding member 105. The flange portion 105a is provided, and the holding member 105 is therefore threaded into the hole portion 63a from the inside of the grip portion 63 to the outside. When the holding member 105 is threaded into the hole portion 63a, the flange portion 105a is caught on the inner side of the grip portion 63. This prevents the cylinder 111 from coming out of the grip portion 63. At the same time, one part of the outer circumferential surface of the holding member 105 abuts on the O-ring 103.

The mouthpiece 107 has a thread groove (not shown in the drawings) provided in the inner circumferential surface of the mouthpiece 107, and the mouthpiece 107 is threaded into the holding member 105. The mouthpiece 107 has the lower flange portion 107a which fits to the upper annular groove portion 63c, and an upper flange portion 107b provided higher than the lower flange portion 107a in the axial direction of the mouthpiece 107. The lower flange portion 107a and the upper flange portion 107b are formed outward in the diametrical direction of the mouthpiece 107. The upper flange portion 107b is provided outside the grip portion 63. When the lower flange portion 107a has fitted to the upper annular groove portion 63c, the flange portion 105a and the lower flange portion 107a vertically catch the grip portion 63 therebetween in the axial direction of the cylinder 111, so that the cylinder 111 is fixed to the grip portion 63.

When the mouthpiece 107 is threaded into the holding member 105, the lower flange portion 107a fits to the upper annular groove portion 63c, and compresses the O-ring 103. This prevents the gas and the liquid from entering the endoscope 1 from the outside. That is, water tightness and airtightness are ensured.

[Piston 121]

Next, the piston 121 is described with reference to FIG. 2A and FIG. 2E.

The piston 121 has a hard piston axial portion 123 which is thinner than the cylinder 111 and which is the main body of the piston 121, and an attachment portion 137 to attach the piston axial portion 123 to the grip portion 63.

[Piston Axial Portion 123]

The piston axial portion 123 has an elongated shape along an axial direction of the piston 121. The piston axial portion 123 is inserted into the cylinder 111, and is movable relative to the cylinder 111 along the axial direction of the cylinder 111. Since the piston axial portion 123 is thinner than the cylinder 111, a flow portion in which a fluid flows is formed between an outer circumferential surface of the piston axial portion 123 and the inner circumferential surface of the cylinder 111.

As shown in FIG. 2E, the piston axial portion 123 has one end portion 123a which is provided to be surrounded by the air/water supply button 69b and which is provided outside the cylinder 111 (the grip portion 63), and the other end portion 123b provided inside the cylinder 111. The one end portion 123a is screwed to, for example, the air/water supply button 69b.

[Communication Path 125 and Through-Hole Portion 127]

As shown in FIG. 2E, the piston axial portion 123 also has a communication path 125 which is provided inside the piston axial portion 123 and which is provided on the central axis of the piston axial portion 123, and a through-hole portion 127 which is provided at the other end portion 123b side of the piston axial portion 123 and which passes through the piston axial portion 123 in a diametrical direction of the piston axial portion 123. The communication path 125 has one end portion 125a which is opening at the one end portion 123a of the piston axial portion 123, and the other end portion 125b which is in communication with the through-hole portion 127. Thus, the communication path 125 is in communication with the outside. The communication path 125 does not pass through the piston axial portion 123, and is in communication with the outside and the through-hole portion 127. The through-hole 127 passes through part of the piston axial portion 123, but does not pass through the entire piston axial portion 123. Thus, although not shown in the drawings, the thickness portion of the piston axial portion 123 is provided around the through-hole portion 127 so that the one end portion 123a and the other end portion 123b may be of the same body.

Figure 4A:
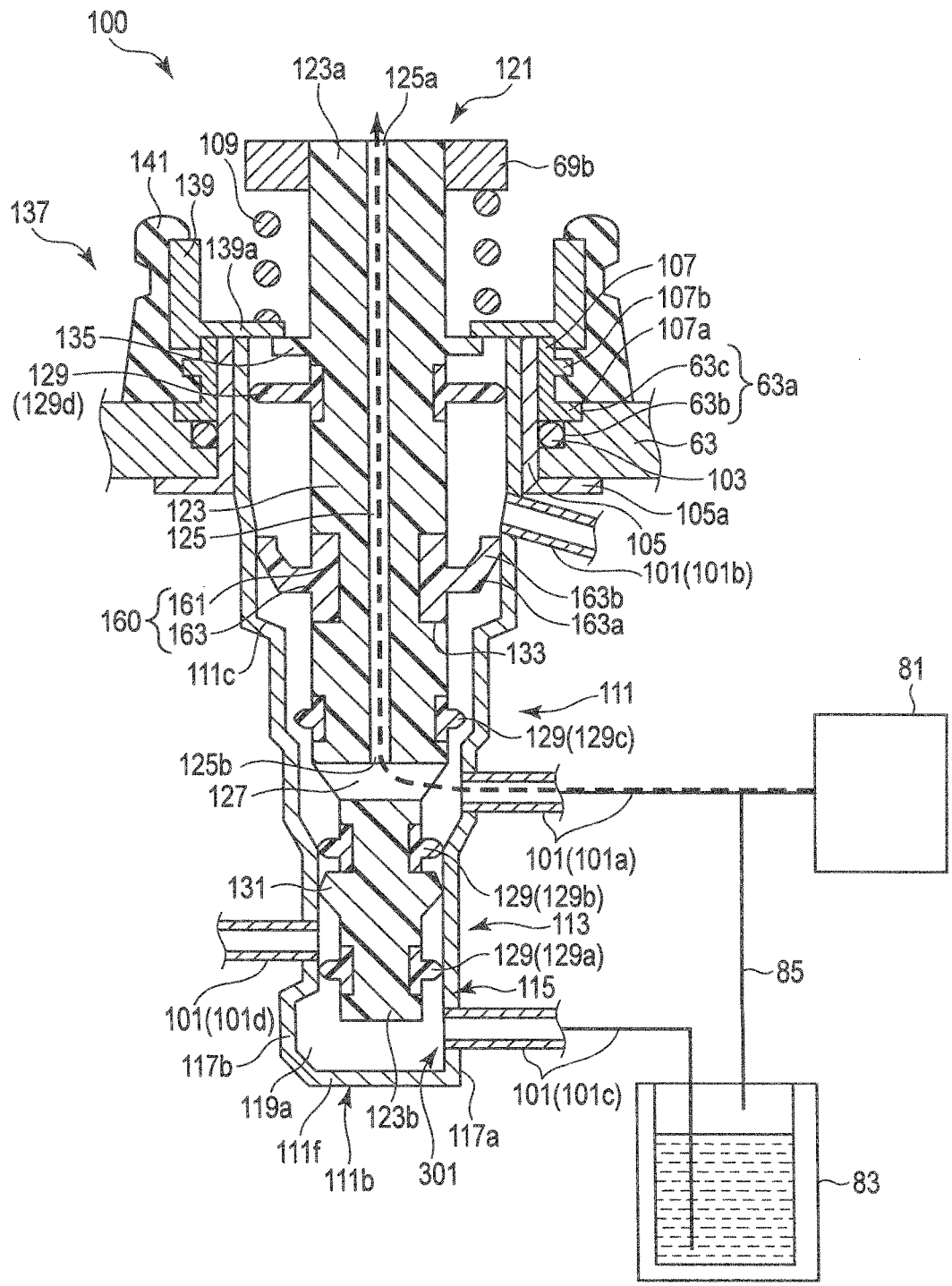
FIG. 4A is a diagram showing the endoscopic channel switching device in a non-operating state.

As shown in FIG. 2A and FIG. 4A, when the one end portion 125a is opening, the communication path 125 and the through-hole portion 127 function as flow portions to discharge, to the outside via the one end portion 125a, the gas supplied into the cylinder 111 from the air supply inlet channel portion 101a.

Figure 4B:
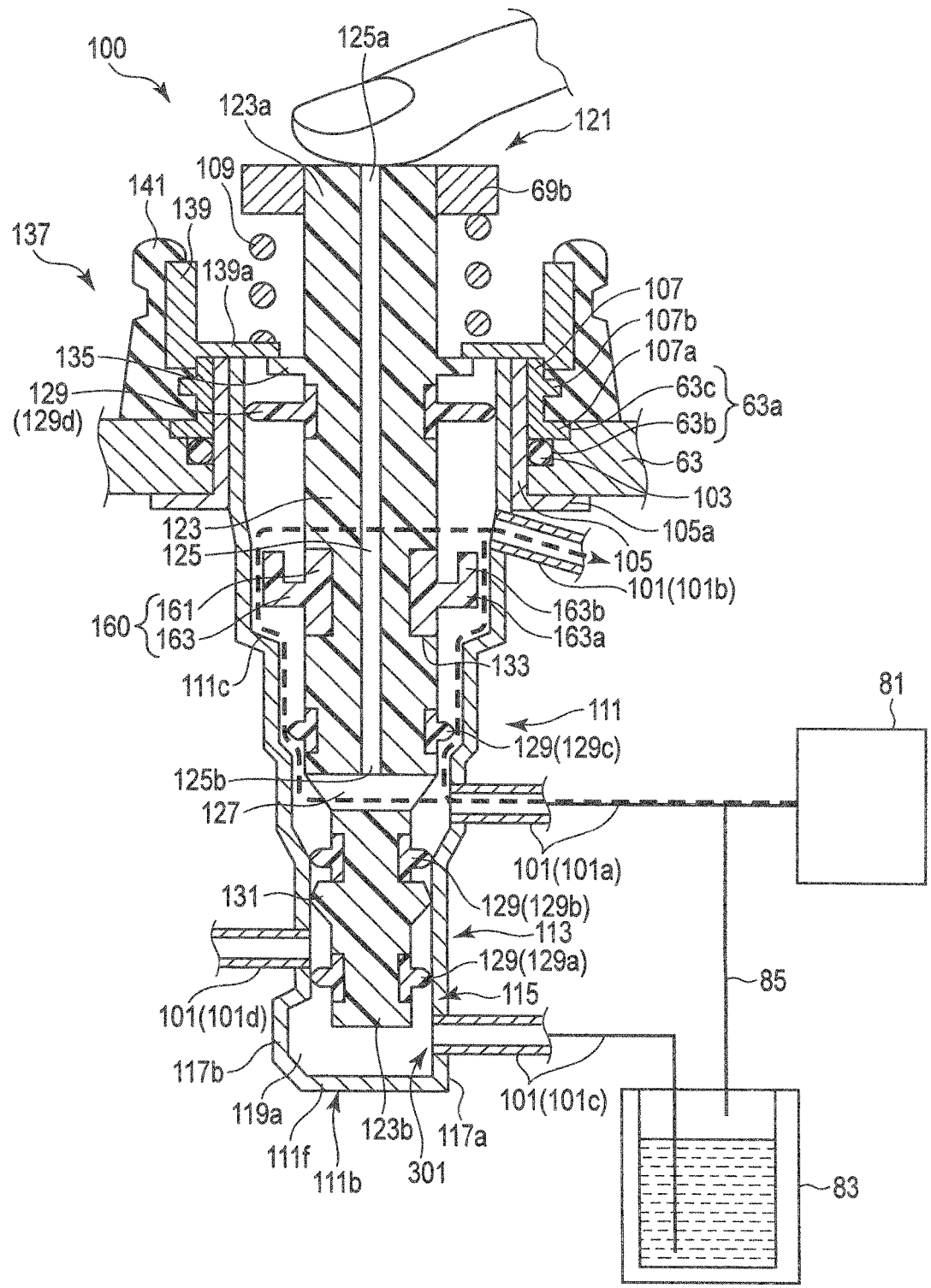
FIG. 4B is a diagram showing the endoscopic channel switching device in an air supplied state.

As shown in FIG. 4B, when the one end portion 125a is blocked by, for example, a finger, the through-hole portion 127 functions as a flow portion to supply, to the air supply outlet channel portion 101b, the gas supplied into the cylinder 111 from the air supply inlet channel portion 101a.

The part of the piston axial portion 123 higher than the through-hole portion 127 is thicker than the part that is lower than the through-hole portion 127. That is, the part of the piston axial portion 123 in which the communication path 125 is provided is thicker than the part in which the communication path 125 is not provided.

[Sealing Member 129]

As shown in FIG. 2A and FIG. 2E, the piston axial portion 123 further has the sealing member 129 which comes into close contact with the inner circumferential surface of the cylinder 111 and seals the space portion between the piston axial portion 123 and the cylinder 111 when the piston axial portion 123 is inserted in the cylinder 111. The sealing member 129 has, for example, packing made of an elastic body such as rubber and elastomer. The sealing member 129 is, for example, ring-shaped.

The sealing member 129 has, for example, the sealing members 129a, 129b, 129c, and 129d. The sealing member 129a is provided, for example, at the other end portion 123b of the piston axial portion 123. The sealing member 129b is provided, for example, between the other end portion 123b of the piston axial portion 123 and the through-hole portion 127 in the axial direction of the piston axial portion 123. The sealing member 129c is provided, for example, between the one end portion 123a of the piston axial portion 123 and the through-hole portion 127 in the axial direction of the piston axial portion 123. The sealing member 129d is provided, for example, closer to the one end portion 123a of the piston axial portion 123 than the sealing member 129c in the axial direction of the piston axial portion 123.

The sealing members 129a and 129b have the same shape each other, and are provided lower than the through-hole portion 127. Thus, the outside diameters of the sealing members 129a and 129b provided in the piston axial portion 123 are the same each other.

The sealing members 129c and 129d are provided higher than the through-hole portion 127. Thus, the outside diameters of the sealing members 129c and 129d provided in the piston axial portion 123 are larger than an outside diameter of the sealing member 129a. The outside diameter of the sealing member 129d is larger than the outside diameter of the sealing member 129c.

The piston axial portion 123 and the sealing member 129 are welded each other so that an interface of the piston axial portion 123 may be in close contact with an interface of the sealing member 129 with no space portion therebetween, so that dirt and bacteria may not adhere to these interfaces, and so that cleaning performance may improve. For this welding, the piston axial portion 123 and the sealing member 129 are formed by, for example, two-color molding or insert molding. The piston axial portion 123 is provided in a die (not shown in the drawings) for molding the sealing member 129. The sealing member 129 is then provided in the die and melted by heat, and this heat melts the surface of the piston axial portion 123. The sealing member 129 is cooled and thereby solidified, and welded to the piston axial portion 123. Thus, the piston axial portion 123 and the sealing member 129 are integrated with each other.

The piston axial portion 123 and the sealing member 129 are cleaned with, for example, a chemical, and are therefore made of chemical resistant materials. The piston axial portion 123 is made of at least one of the substances selected from the group consisting of, for example, polypropylene, polycarbonate, nylon, a sulfonic resin such as polysulfone or polyphenyl sulfone, a liquid crystal polymer, modified polyphenylene ether, and polyether-ether-ketone. The sealing member 129 is made of at least one of the substances selected from the group consisting of, for example, silicon rubber and styrene or olefin elastomer.

[Guide Member 131 and Cutout Portion 133 and Drop Prevention Portion 135]

As shown in FIG. 2E, the piston axial portion 123 also has a guide member 131 provided between the sealing member 129a and the sealing member 129b in the axial direction of the piston axial portion 123, and a cutout portion 133 provided between the sealing member 129c and the sealing member 129d in the axial direction of the piston axial portion 123. The piston axial portion 123 further has a drop prevention portion 135 provided closer to the one end portion 123a than the sealing member 129d in the axial direction of the piston axial portion 123.

[Guide Member 131]

The guide member 131 is integral with the piston axial portion 123. The guide member 131 abuts on, for example, the inner circumferential surface of the cylinder 111 in the minimum diameter portion 113 to prevent the piston axial portion 123 from moving relative to the cylinder 111 in the diametrical direction of the cylinder 111. Thus, the guide member 131 guides the piston axial portion 123 so that the piston axial portion 123 can only move the cylinder 111 along the axial direction of the cylinder 111 when the piston axial portion 123 is inserted in the cylinder 111. The guide member 131 slides on the inner circumferential surface of the cylinder 111 along the axial direction of the cylinder 111 when the piston axial portion 123 is inserted into the cylinder 111.

[Cutout Portion 133]

The cutout portion 133 is circular-ring-shaped. A later-described check valve unit 160 is provided in the cutout portion 133.

[Drop Prevention Portion 135]

The drop prevention portion 135 is, for example, ring-shaped, and is integral with the piston axial portion 123. The drop prevention portion 135 abuts on a bottom portion surface 139a of a later-described drop prevention abutment portion 139 provided in the attachment portion 137.

[Attachment Portion 137]

As shown in FIG. 2E, the attachment portion 137 is provided at the one end portion 123a side of the piston axial portion 123. The attachment portion 137 has the hard drop prevention abutment portion 139 which has a circular cylindrical shape and through which the piston axial portion 123 is inserted and which is provided around the one end portion 123a side of the piston axial portion 123, and a soft attachment main body 141 which has a circular cylindrical shape and which is provided around the drop prevention abutment portion 139.

[Drop Prevention Abutment Portion 139]

The drop prevention abutment portion 139 is provided in close contact with the entire inner circumferential surface of the attachment main body 141. The drop prevention abutment portion 139 has a circular cylindrical shape with the bottom portion surface 139a on one side. The bottom portion surface 139a has an insertion hole portion 139b through which the piston axial portion 123 is inserted. The bottom portion surface 139a abuts on the drop prevention portion 135. In the axial direction of the piston 121, the bottom portion surface 139a is provided lower of the air/water supply button 69b. When the channel switching device 100 is assembled, the bottom portion surface 139a abuts on the one end portion 111a of the cylinder 111, an edge portion of the holding member 105, and an edge portion of the mouthpiece 107 as shown in FIG. 2A.

[Urging Member 109]

An urging member 109 is provided between the bottom portion surface 139a and the air/water supply button 69b in the axial direction of the piston 121. The urging member 109 is provided to wind around the side of the one end portion 123a of the piston axial portion 123. The urging member 109 has, for example, a metallic spiral spring. The urging member 109 is capable of expansion and contraction in the axial direction of the piston 121. The urging member 109 has an urging force to urge the piston axial portion 123 upward via the air/water supply button 69b and to urge the drop prevention abutment portion 139 (the bottom portion surface 139a) downward (the drop prevention portion 135). When the urging member 109 is in its natural state, the urging member 109 urges the piston axial portion 123 upward via the air/water supply button 69b, and urges the drop prevention abutment portion 139 (the bottom portion surface 139a) downward (the drop prevention portion 135). At the same time, the drop prevention portion 135 and the bottom portion surface 139a abut on and press each other. Thus, the drop prevention portion 135 prevents the piston axial portion 123 from coming off the attachment portion 137. The urging member 109 is surrounded by the drop prevention abutment portion 139.

[Attachment Main Body 141]

The attachment main body 141 is made of a soft material such as rubber. The attachment main body 141 is engaged with the upper flange portion 107b of the mouthpiece 107, and provided on the outer circumferential surface of the grip portion 63.

[Check Valve Unit 160]

As shown in FIG. 2A and FIG. 2E, the channel switching device 100 has the check valve unit 160 provided in the cutout portion 133 of the piston 121.

The check valve unit 160 opens and closes in response to the pressure inside the cylinder 111, and comes in and out of close contact with the inner circumferential surface of the cylinder 111 in response to the opening and closing. The check valve unit 160 seals the space portion between the cylinder 111 and the piston axial portion 123 by close contact. The check valve unit 160 is provided in the piston axial portion 123 via the cutout portion 133, and moves together with the piston axial portion 123 in accordance with the movement of the piston axial portion 123 relative to the cylinder 111. The check valve unit 160 has an umbrella-like shape.

This check valve unit 160 has a main body 161 having a circular cylindrical shape to fill the cutout portion 133, and a check valve portion 163 which has a cylindrical shape decreasing in diameter downward along the central axis C and which is continuously connected to the main body 161 to be integral with the main body 161 in the lower part.

The main body 161 and the check valve portion 163 are made of an elastic material such as rubber and elastomer similar to the sealing member 129. The main body 161 and the check valve portion 163 are integral with each other.

[Main Body 161]

The main body 161 fills the cutout portion 133, and is bonded to the piston axial portion 123. Thus, when the piston axial portion 123 moves relative to the cylinder 111, the main body 161 moves together with the piston axial portion 123.

As shown in FIG. 2A and FIG. 2E, an outside diameter of the main body 161 is essentially the same as the outside diameter of the piston axial portion 123. Thus, when the main body 161 is filling the cutout portion 133, an outer circumferential surface of the main body 161 is flush with the outer circumferential surface of the piston axial portion 123.

[Check Valve Portion 163]

As shown in FIG. 2A and FIG. 2E, the check valve portion 163 has a shape which is essentially closed downward and essentially open upward. This shape represents one of the shapes selected from the group consisting of, for example, an essentially umbrella-like shape, a hollow truncated-cone shape, a semispherical domed shape, and a hollow parabolic shape. Thus, the check valve portion 163 gradually decreases in diameter from the side of an upper end portion 163b of the check valve portion 163 to the side of a lower end portion 163a of the check valve portion 163 in a axial direction of the check valve portion 163.

As shown in FIG. 2A and FIG. 2E, the check valve portion 163 has the lower end portion 163a which is provided in the lower part of the check valve portion 163 and which is essentially closed, and the upper end portion 163b which is provided in the upper part of the check valve portion 163 and which is essentially open upward. The lower end portion 163a and the upper end portion 163b have hollow shapes, and are ring-shaped.

As shown in FIG. 2A and FIG. 2E, the lower end portion 163a is integral with the lower end portion side of the outer circumferential surface of the main body 161, and is fixed to the lower end portion side of the outer circumferential surface of the main body 161. Thus, the check valve portion 163 is integral with the main body 161. The lower end portion 163a functions as the root portion of the check valve portion 163, functions as a fixed end portion, and functions as a closed end portion.

As shown in FIG. 4A and FIG. 4B, the upper end portion 163b opens and closes in response to the pressure inside the cylinder 111, and comes in and out of close contact with the inner circumferential surface of the cylinder 111 in response to the opening portion and closing. The upper end portion 163b seals the space portion between the cylinder 111 and the piston axial portion 123 by close contact. Thus, the upper end portion 163b functions as a distal end portion of the check valve portion 163, functions as a free end portion, and functions as an open end portion. The side of the upper end portion 163b has uniform strength in a circumferential direction of the check valve unit 160. In this case, the thickness does not vary on the side of the upper end portion 163b. In this case, the side of the upper end portion 163b has uniform thickness in a circumferential direction of the check valve unit 160.

As described above, the main body 161 is bonded to the piston axial portion 123, and the check valve portion 163 is integral with the main body 161. Therefore, as shown in FIG. 4A and FIG. 4C, when the piston axial portion 123 moves relative to the cylinder 111, the check valve portion 163 including the main body 161 moves together with the piston axial portion 123. When the state switches from the state shown in FIG. 4A to the state shown in FIG. 4C and the lower end portion 163a moves downward, the lower end portion 163a functions as a head (distal) portion of the check valve unit 160. When the state switches from the state shown in FIG. 4C to the state shown in FIG. 4A and the upper end portion 163b moves upward, the upper end portion 163b functions as a head (distal) portion of the check valve unit 160. In particular, when the state switches from, for example, a later-described water supplied state shown in FIG. 4C to a non-operating state shown in FIG. 4A, the upper end portion 163b slides upward on the inner circumferential surface of the cylinder 111 because the upper end portion 163b is in close contact with the inner circumferential surface of the cylinder 111. Thus, the upper end portion 163b functions as the head portion of the check valve unit 160 which slides upward.

The front surface of the check valve portion 163 faces toward the other end portion 123b and the back surface of the check valve portion 163 faces toward the one end portion 123a so that the lower end portion 163a of the check valve portion 163 is provided on the side of the other end portion 123b and the upper end portion 163b of the check valve portion 163 is provided on the side of the one end portion 123a.

As shown in FIG. 2A, FIG. 4A and FIG. 4B, in the natural state of the check valve unit 160, the upper end portion 163b of the check valve portion 163 is closed by pressure and separated from the inner circumferential surface of the cylinder 111, and then the check valve portion 163 is opened and the upper end portion 163b of the check valve portion 163 comes into close contact with the inner circumferential surface of the cylinder 111. In this situation, the check valve portion 163 has a thickness such that the check valve portion 163 does not abut on the outer circumferential surface of the main body 161.

In the natural state of the check valve unit 160, an outside diameter of the side of the upper end portion 163b is uniform. In the natural state of the check valve unit 160, an inside diameter of the side of the upper end portion 163b is also uniform.

An edge portion of the upper end portion 163b of the check valve portion 163 is, in its natural state, larger than the inside diameter of the cylinder ill. Therefore, when the piston axial portion 123 is inserted in the cylinder 111, the edge portion of the upper end portion 163b of the check valve portion 163 is compressed by the cylinder 111, and thereby comes into close contact with the inner circumferential surface of the cylinder 111, as shown in FIG. 2A, FIG. 4A and FIG. 4B. As a result, the check valve portion 163 seals the space portion between the cylinder 111 and the piston axial portion 123.

As shown in FIG. 4B, if the one end portion 125a of the communication path 125 is blocked by, for example, a finger while the gas is supplied into the cylinder 111 from the air supply inlet channel portion 101a, the pressure inside the cylinder 111 rises, and the upper end portion 163b of the check valve portion 163 closes and then separates from the inner circumferential surface of the cylinder 111. At the same time, the space portion between the cylinder 111 and the piston axial portion 123 functions as a flow portion to supply, to the air supply outlet channel portion 101b, the gas supplied into the cylinder 111 from the air supply inlet channel portion 101a.

In this way, the upper end portion 163b opens and closes in response to the pressure inside the cylinder 111, and thereby comes in and out of close contact with the inner circumferential surface of the cylinder 111.

The check valve unit 160 opens and closes in response to the pressure inside the cylinder 111. When the check valve unit 160 closes, the upper end portion 163b of the check valve unit 160 separates from the inner circumferential surface of the cylinder 111. When the check valve unit 160 opens, the upper end portion 163b of the check valve portion 163 circumferentially comes into close contact with the inner circumferential surface of the cylinder 111, and thereby seals the space portion between the cylinder 111 and the piston 121.

[Manufacturing Method of Cylinder 111]

Next, a manufacturing method of the cylinder 111 according to the present embodiment is described with reference to FIG. 3A, FIG. 3B, FIG. 3C, and FIG. 3D.

A thin plate is subjected to the deep-draw stepped pressing process so that the opening portion 111d and the bottom portion 111f may be provided. As a result, the tapered cylinder 111 having the opening portion 111d and the bottom portion 111f is formed.

One part of the circumferential surface of the cylinder 111 located in the lowermost part of the minimum diameter portion 113 is then bulged to form the partial diameter increased portion 117b. The unbulged other part of the circumferential surface of the cylinder 111 located in the lowermost part of the minimum diameter portion 113 functions as the minimum diameter uniform portion 117a. Thus, as shown in FIG. 3A, the tapered cylinder 111 having the abutment surface 111c, the opening portion 111d, the bottom portion 111f, the minimum diameter portion 113, the blocked end portion 115, the minimum diameter uniform portion 117a, and the partial diameter increased portion 117b is formed.

The connection of the minimum diameter uniform portion 117a and the water supply inlet channel portion 101c is briefly described below.

Figure 3A:
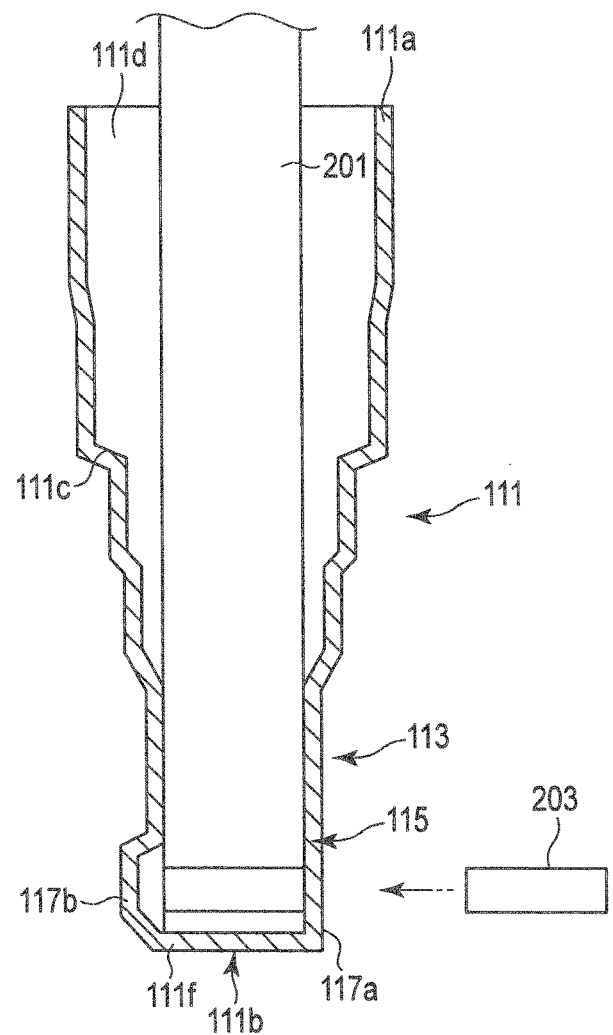
FIG. 3A is a diagram showing how a side surface hole portion is formed by a pressing process in a circumferential surface of the cylinder in a minimum diameter uniform portion in a situation where a thin plate is subjected to a deep-draw stepped pressing process so that an opening portion and a bottom portion will be provided, and the tapered cylinder having the opening portion, the bottom portion, a minimum diameter portion, the blocked end portion, the minimum diameter uniform portion, and a partial diameter increased portion is formed.
Figure 3B:
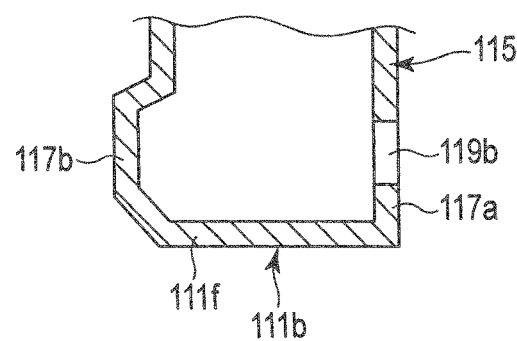
FIG. 3B is a diagram showing the side surface hole portion formed by the pressing process.

As shown in FIG. 3A, for example, a die 201 such as a jig is inserted into the cylinder 111 from the opening portion 111d. An outside diameter of the die 201 is essentially the same as the inside diameter of the minimum diameter portion 113. Thus, a circumferential surface of the die 201 is simultaneously touched on the inner circumferential surface of the cylinder 111 in the minimum diameter uniform portion 117a and the minimum diameter portion 113. In the minimum diameter uniform portion 117a, a punch 203 is then pressed from an outside of the cylinder 111 toward the die 201. Thus, as shown in FIG. 3B, a side surface hole portion 119b is formed in the circumferential surface of the cylinder 111 in the minimum diameter uniform portion 117a.

The end portion of the water supply inlet channel portion 101c then passes through the side surface hole portion 119b, and is provided inside the cylinder 111. The water supply inlet channel portion 101c is joined to the cylinder 111, for example, by welding, and is thereby coupled to the cylinder 111. Therefore, the coupling part 301 between the water supply inlet channel portion 101c and the cylinder 111 is provided in the circumferential surface of the cylinder 111 in the minimum diameter uniform portion 117a.

The part of the end portion of the water supply inlet channel portion 101c inserted in the cylinder 111 is cut and removed by a tool (not shown in the drawings).

Figure 3C:
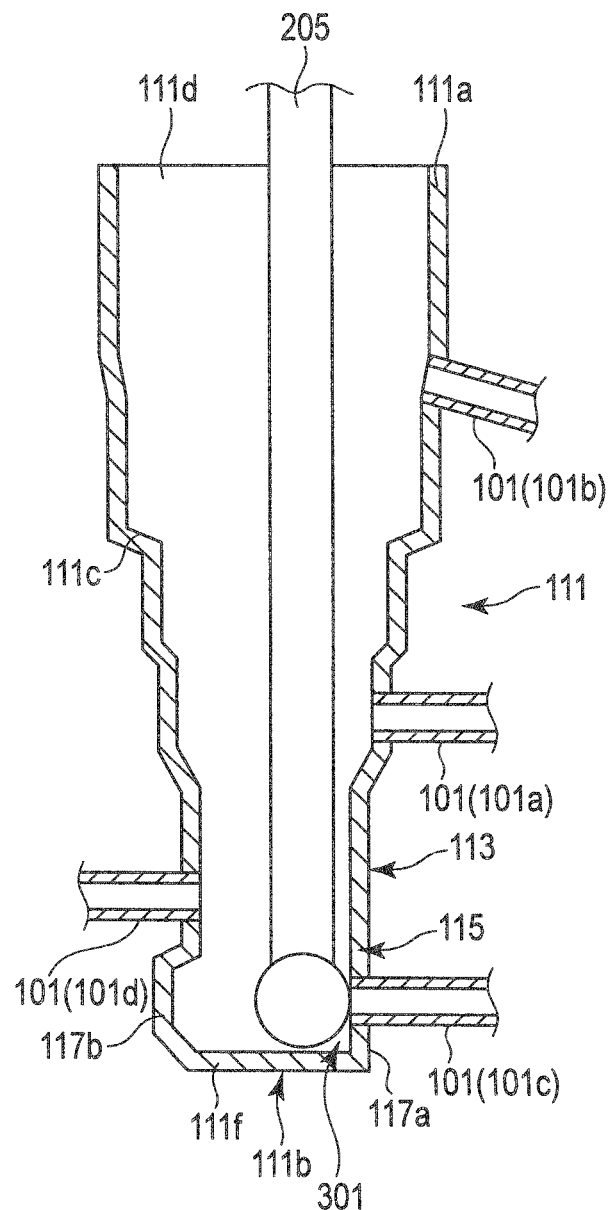
FIG. 3C is a diagram showing how a channel portion is joined to the side surface hole portion shown in FIG. 3B and coupled to the cylinder, a coupling part between the channel portion and the cylinder is provided in the minimum diameter uniform portion, and the coupling part is finished by a machine tool.

As shown in FIG. 3C, a machine tool 205 is then inserted into the cylinder 111 from the opening portion 111d. The coupling part 301 between the water supply inlet channel portion 101c and the cylinder 111 is then finished, for example, cut from the inside of the cylinder 111 by the machine tool 205. As a result, unevenness (not shown in the drawings) in the coupling part 301 is cut, the coupling part 301 is smoothed, and the coupling part 301 smoothly continues to the inner circumferential surface of the cylinder 111 in the minimum diameter uniform portion 117a. The coupling part 301 is provided in the minimum diameter uniform portion 117a, and is therefore provided flush with one part of the minimum diameter portion 113 in the axial direction of the cylinder 111.

Figure 3D:
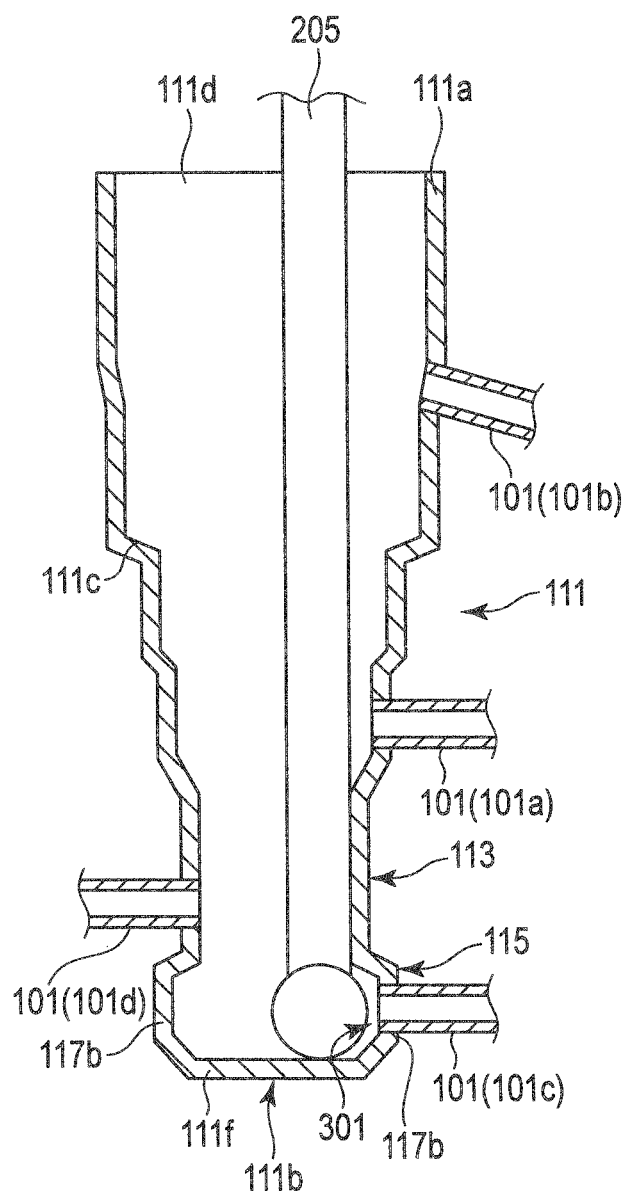
FIG. 3D is a diagram showing how the coupling part between the channel portion and the cylinder is provided in the partial diameter increased portion in contrast with the present embodiment, and the coupling part is finished by the machine tool.

As shown in FIG. 3D, for example, if the coupling part 301 between the water supply inlet channel portion 101c and the cylinder 111 is provided in the partial diameter-increased portion 117b, the coupling part 301 is provided outside the minimum diameter portion 113 in the diametrical direction of the cylinder 111.

In this case, when the part of the end portion of the water supply inlet channel portion 101c inserted in the cylinder 111 is cut by a tool (not shown in the drawings), a special dedicated tool is produced, and the dedicated tool processes this part. As a result, time and costs are incurred to process the end portion of the water supply inlet channel portion 101c so that it does not remain inside the cylinder 111, and the processing is difficult.

In this case, as shown in FIG. 3D, the machine tool 205 does not easily reach the coupling part 301, and finishing such as the above-mentioned cutting may not be easily performed. As a result, the unevenness may not be completely removed, and the coupling part 301 may not be smoothed. Even if the machine tool 205 reaches the coupling part 301, time and costs may be incurred to smooth the coupling part 301.

The size of the machine tool 205 is influenced by the size of the partial diameter increased portion 117b.

This may require dedicated tools for removal and finishing, and lead to an increase in costs, processing, and lead times.

However, according to the present embodiment, as shown in FIG. 3C, the coupling part 301 between the water supply inlet channel portion 101c and the cylinder 111 is not provided outside the minimum diameter portion 113 in the diametrical direction of the cylinder 111, and is provided flush with the minimum diameter portion 113 in the axial direction of the cylinder 111. Thus, the tool (not shown in the drawings) and the machine tool 205 easily reach unremoved parts and the coupling part 301, and the above-mentioned removal and finishing are easily performed. As a result, the removal can be reliably conducted, any unevenness is completely removed, and the coupling part 301 is machined smooth. This ensures that the machine tool 205 reaches the coupling part 301, and the size of the machine tool 205 is influenced by the size of the partial diameter increased portion 117b.

This eliminates the need for dedicated tools for the removal and finishing, and leads to decreased costs, no increase in processes, and decreased lead times.

Although the water supply inlet channel portion 101c has been described above, the same also essentially applies to the other channel portions 101.

[Assembly Method]

Next, an assembly method of the channel switching device 100 according to the present embodiment is described with reference to FIG. 2A and FIG. 2E.

(Step 1—FIG. 2E)

As shown in FIG. 2E, the attachment portion 137 is assembled so that the drop prevention abutment portion 139 comes into close contact with the entire inner circumferential surface of the attachment main body 141.

The attachment portion 137 is then attached to the piston axial portion 123 so that the piston axial portion 123 may be inserted through the insertion hole portion 139b in the bottom portion surface 139a, and the bottom portion surface 139a of the drop prevention abutment portion 139 may abut on the drop prevention portion 135.

The one end portion 123a is then screwed to the air/water supply button 69b so that the urging member 109 may wind around the side of the one end portion 123a of the piston axial portion 123 and the urging member 109 may be provided between the bottom portion surface 139a and the air/water supply button 69b. At the same time, the urging member 109 urges the piston axial portion 123 upward via the air/water supply button 69b, and urges the drop prevention abutment portion 139 (the bottom portion surface 139a) downward (the drop prevention portion 135). The drop prevention portion 135 and the bottom portion surface 139a of the drop prevention abutment portion 139 abut on and press each other.

Consequently, the piston 121 is assembled.

The assembly of the attachment portion 137 and the assembly of the piston 121 do not need to be limited to the above.

In Step 1, the check valve portion 163 is in its natural state.

(Step 2—FIG. 2A)

As shown in FIG. 2A, the piston axial portion 123 is then pressed into the cylinder 111 so that the upper flange portion 107b may be engaged with the attachment main body 141, the attachment main body 141 may abut on the outer circumferential surface of the grip portion 63, the bottom portion surface 139a of the drop prevention abutment portion 139 may abut on the one end portion 111a of the cylinder 111, the edge portion of the holding member 105, and the edge portion of the mouthpiece 107, and the check valve unit 160 may be provided between the abutment surface 111c and the air supply outlet channel portion 101b in the axial direction of the channel switching device 100. Consequently, the channel switching device 100 is assembled.

Step 2 shows one of the non-operating state in which air supply and water supply are not performed and the channel switching device 100 is not operated, and an air supplied state in which the channel switching device 100 is operated and air supply is performed.

[Operating Method]

Next, an operating method of the channel switching device 100 including the check valve unit 160 according to the present embodiment is described with reference to FIG. 4A, FIG. 43, and FIG. 4C. FIG. 4A corresponds to Step 2 and FIG. 2A.

[Non-Operating State]

The non-operating state shown in Step 2 is described with reference to FIG. 4A.

As shown in FIG. 4A, the sealing member 129d is provided higher than the air supply outlet channel portion 101b, is in close contact with the inner circumferential surface of the cylinder 111, and seals the space portion between the cylinder 111 and the piston axial portion 123. The check valve unit 160 is provided between the abutment surface 111c and the air supply outlet channel portion 101b. The check valve portion 163 is opening, and the upper end portion 163b of the check valve portion 163 is in close contact with the inner circumferential surface of the cylinder 111, and seals the space portion between the cylinder 111 and the piston axial portion 123. Therefore, the internal space portion of the cylinder 111 on the side of the air supply outlet channel portion 101b is sealed by the sealing member 129d and the check valve portion 163.

The sealing members 129a and 129b are in close contact with the inner circumferential surface of the cylinder 111 in, for example, the minimum diameter portion 113, and seal the space portion between the cylinder 111 and the piston axial portion 123. The sealing member 129a is provided between the water supply inlet channel portion 101c and the water supply outlet channel portion 101d. The sealing member 129b is provided between the water supply outlet channel portion 101d and the air supply inlet channel portion 101a. Thus, the internal space portion of the cylinder 111 on the side of the water supply inlet channel portion 101c (the blocked end portion 115) is sealed by the sealing member 129a. The internal space portion of the cylinder 111 on the side of the water supply outlet channel portion 101d is sealed by the sealing members 129a and 129b.

The one end portion 125a is opening, and the communication path 125 is in communication with the outside. As described above, the upper end portion 163b of the check valve portion 163 is in close contact with the inner circumferential surface of the cylinder 111, and the sealing member 129b is in close contact with the inner circumferential surface of the cylinder 111. Thus, the air supply inlet channel portion 101a is in communication with the outside via the through-hole portion 127 and the communication path 125. Therefore, the gas is supplied from the air supply device 81, and discharged to the outside via the air supply inlet channel portion 101a, the through-hole portion 127, and the communication path 125.

The sealing member 129c is provided between the air supply inlet channel portion 101a and the air supply outlet channel portion 101b, is separate from the inner circumferential surface of the cylinder 111, and does not seal the space portion between the cylinder 111 and the piston axial portion 123.

[Switch from Non-Operating State to Air Supplied State]

Next, the air supplied state shown in Step 2 is described with reference to FIG. 4B.

The grip portion 63 is held by the operator from the state shown in FIG. 4A. As shown in FIG. 4B, the one end portion 125a, which is opening, is blocked by the finger of the operator. The gas supplied into the cylinder 111 and the communication path 125 from the air supply inlet channel portion 101a fills the cylinder 111 including the communication path 125. At the same time, the gas also flows to the side of the check valve portion 163. Since the one end portion 125a is blocked, the pressure rises inside the cylinder 111. Accordingly, the check valve portion 163 closes in response to the pressure rise.

At the same time, as shown in FIG. 4B, the upper end portion 163b of the check valve portion 163 separates from the inner circumferential surface of the cylinder 111.

Therefore, as shown in FIG. 4B, the gas flows into the internal space portion of the cylinder 111 on the side of the air supply outlet channel portion 101b, through the space portion between the check valve portion 163 and the cylinder 111 and the space portion between the piston axial portion 123 and the cylinder 111.

At the same time, the sealing members 129b and 129d keep sealing the space portion between the cylinder 111 and the piston axial portion 123. The sealing member 129c is separated from the inner circumferential surface of the cylinder 111. Therefore, the gas flows to the air supply outlet channel portion 101b, and is discharged to the outside from the air/water supply nozzle.

[Switch from Air Supplied State to Water Supplied State]

Next, the water supplied state is described with reference to FIG. 4C.

The air/water supply button 69b is pressed by the finger of the operator while the one end portion 125a is blocked by the finger of the operator. As a result, the urging member 109 is contracted, and the piston axial portion 123 is pressed into the cylinder 111. At the same time, the piston axial portion 123 makes a large movement downward relative to the cylinder 111. The drop prevention portion 135 separates from the bottom portion surface 139a of the drop prevention abutment portion 139.

The sealing member 129d slides downward on the inner circumferential surface of the cylinder 111. The sealing member 129d is provided higher than the air supply outlet channel portion 101b, and seals the space portion between the cylinder 111 and the piston axial portion 123.

The sealing member 129c moves downward in response to the movement of the piston axial portion 123. The sealing member 129c then comes into close contact with the inner circumferential surface of the cylinder 111 between the air supply inlet channel portion 101a and the air supply outlet channel portion 101b, and seals the space portion between the cylinder 111 and the piston axial portion 123.

Thus, the internal space portion of the cylinder 111 on the side of the air supply outlet channel portion 101b is sealed by the sealing members 129c and 129d.

The sealing member 129b slides downward on the inner circumferential surface of the cylinder 111 in response to the movement of the piston axial portion 123. The sealing member 129b is provided lower than the air supply inlet channel portion 101a and higher than the water supply outlet channel portion 101d, and seals the space portion between the cylinder 111 and the piston axial portion 123.

Thus, the internal space portion of the cylinder 111 on the side of the air supply inlet channel portion 101a is sealed by the sealing members 129b and 129c.

The sealing member 129a moves downward in response to the movement of the piston axial portion 123. At the same time, one part of the sealing member 129a slides on the inner circumferential surface of the cylinder 111 in the minimum diameter uniform portion 117a, and remains in close contact with this inner circumferential surface. Since the partial diameter increased portion 117b bulges out of the minimum diameter portion 113 in the diametrical direction of the cylinder 111, the other part of the sealing member 129a is separate from the inner circumferential surface of the cylinder 111 in the partial diameter increased portion 117b, and is out of abutment and out of close contact with the inner circumferential surface. Therefore, the clearance portion 119a is formed between this inner circumferential surface and the other part of the sealing member 129a. Thus, the sealing member 129a does not seal the space portion between the cylinder 111 and the piston axial portion 123.

Thus, the water supply inlet channel portion 101c communicates with the water supply outlet channel portion 101d through the internal space portion of the cylinder 111 provided lower than the sealing member 129b. The gas is then supplied to the water supply device 83 from the air supply device 81 via the channel portion 85. If the internal pressure of the water supply device 83 increases, the liquid filling the water supply device 83 flows to the water supply inlet channel portion 101c. The liquid then flows to the water supply outlet channel portion 101d from the water supply inlet channel portion 101c through the internal space portion of the cylinder 111 provided lower than the sealing member 129b. As a result, the liquid is discharged to the outside from the air/water supply nozzle.

The gas which has flowed from the air supply device 81 also flows into the cylinder 111 through the air supply inlet channel portion 101a. However, the sealing members 129b and 129c seal the internal space portion of the cylinder 111 on the side of the air supply inlet channel portion 101a, and this therefore ensures that the gas flows to the water supply device 83.

In the water supplied state, the sealing member 129c seals the internal space portion of the cylinder 111 on the side of the air supply outlet channel portion 101b, so that the gas does not flow into the internal space portion of the cylinder 111 on the side of the air supply outlet channel portion 101b. Thus, when the channel switching device 100 switches from the air supplied state shown in FIG. 4B to the water supplied state shown in FIG. 4C, the gas remaining in the internal space portion of the cylinder 111 on the side of the air supply outlet channel portion 101b continues to be discharged from the air supply outlet channel portion 101b. As a result, the pressure in the internal space portion on the side of the air supply outlet channel portion 101b decreases.

When the channel switching device 100 switches from the air supplied state shown in FIG. 4B to the water supplied state shown in FIG. 4C, the check valve unit 160 moves in response to the movement of the piston axial portion 123 while the check valve portion 163 is closed as shown in FIG. 4B. At the same time, the check valve portion 163 opens in response to the pressure drop. The upper end portion 163b of the check valve portion 163 then comes into close contact with the inner circumferential surface of the cylinder 111.

When the channel switching device 100 switches from the air supplied state shown in FIG. 4B to the water supplied state shown in FIG. 4C, the check valve portion 163 moves downward with the tapered lower end portion 163a at the head. Thus, the check valve portion 163 moves without being turned up.

[Switch from Water Supplied State to Non-Operating State]

If the finger of the operator separates from the one end portion 125a, the air/water supply button 69b is released. Thus, the urging member 109 expands, and the piston axial portion 123 is raised relative to the cylinder 111 via the air/water supply button 69b. At the same time, as shown in FIG. 4A, the piston axial portion 123 makes a large movement upward relative to the cylinder 111 until the drop prevention portion 135 abuts on a bottom portion surface 139a of a drop prevention abutment portion 139.

The sealing members 129a, 129b, 129c, and 129d move upward in response to the movement of the piston axial portion 123, and are provided at the positions described in the non-operating state shown in FIG. 4A.

The check valve unit 160 also moves upward in response to the movement of the piston axial portion 123. At the same time, as has been described in the water supplied state shown in FIG. 4C, the check valve portion 163 is open, and the upper end portion 163b of the check valve portion 163 is in close contact with the inner circumferential surface of the cylinder 111. Therefore, when the check valve unit 160 moves upward, the upper end portion 163b of the check valve portion 163 slides upward on the inner circumferential surface of the cylinder 111.

[Cleaning of Channel Switching Device 100]

Next, cleaning of the channel switching device 100 is described.

The piston 121 is removed from the cylinder 111 and cleaned. In this instance, the outer circumferential surface of the piston axial portion 123, the communication path 125, and the through-hole portion 127 are not covered by the check valve portion 163, and is reliably exposed as shown in FIG. 2E. Thus, a cleaning solution flows to these components without being affected by the check valve portion 163.

As described above, the coupling part 301 between the water supply inlet channel portion 101c and the cylinder 111 is not provided outside the minimum diameter portion 113 in the diametrical direction of the cylinder 111, and is provided flush with the minimum diameter portion 113 in the axial direction of the cylinder 111. The coupling part 301 smoothly continues to the inner circumferential surface of the cylinder 111 in the minimum diameter uniform portion 117a. Therefore, when the cylinder 111 is cleaned, the cleaning solution and a cleaning brush easily reach the coupling part 301, and cleaning performance in the coupling part 301 improves.

Advantageous Effects

Thus, according to the present embodiment, the minimum diameter uniform portion 117a is provided lower than the minimum diameter portion 113, is provided flush with the minimum diameter portion 113 in the axial direction of the cylinder 111, and is coupled to the water supply inlet channel portion 101c. Therefore, according to the present embodiment, a tool (not shown in the drawings) and the machine tool 205 can easily reach unremoved parts and the coupling part 301, the removal and finishing are easily performed, and the coupling part 301 can be smoothed. Thus, according to the present embodiment, dedicated tools for the removal and finishing can become unnecessary, which can lead to decreased costs, no increase in processes, decreased lead times, and improved cleaning performance.

According to the present embodiment, the minimum diameter uniform portion 117a is provided, and the partial diameter increased portion 117b alone is increased in diameter, so that the increase in the diameter of the whole blocked end portion 115 can be prevented.

According to the present embodiment, the minimum diameter uniform portion 117a and the partial diameter increased portion 117b are provided flush with each other in the plane that intersects at right angles with the axial direction of the cylinder 111. Thus, according to the present embodiment, the entire length of the cylinder 111 can be shorter than when the minimum diameter uniform portion 117a and the partial diameter increased portion 117b are provided in parallel along the axial direction of the cylinder 111.

According to the present embodiment, the cylinder 111 having the minimum diameter uniform portion 117a and the partial diameter increased portion 117b can be formed from a thin plate, so that the cylinder 111 can be lighter.

According to the present embodiment, L1≥L2. Thus, according to the present embodiment, the strength of the coupling part 301 between the water supply inlet channel portion 101c and the cylinder 111 can be ensured.

According to the present embodiment, the inner circumferential surface of the cylinder 111 in the partial diameter increased portion 117b is always out of close contact with the sealing member 129a so that the clearance portion 119a may be formed. Thus, according to the present embodiment, the flow portion can always be ensured.

According to the present embodiment, the minimum diameter uniform portion 117a has only to be provided in, for example, the coupling part 301 between the water supply inlet channel portion 101c and the cylinder 111 which is a channel portion provided lower than the minimum diameter portion 113 and provided in the lowermost part.

Although one minimum diameter uniform portion 117a and one partial diameter increased portion 117b are only provided, the present invention does not need to be limited to this. More than one minimum diameter uniform portion 117a and more than one partial diameter increased portion 117b may be provided. In this case, the minimum diameter uniform portions 117a and the partial diameter increased portions 117b may be alternately provided in the circumferential direction of the cylinder 111.

The minimum diameter portion 113 has a circular cylindrical shape, the minimum diameter uniform portions 117a follows one part of the minimum diameter portion 113, and the partial diameter increased portion 117b is C-shaped. However, the present invention does not need to be limited to this. The minimum diameter portion 113 may have a rectangular shape, the minimum diameter uniform portions 117a may follow one part of the minimum diameter portion 113, and the partial diameter increased portion 117b has only to be larger than the minimum diameter portion 113.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic channel switching device comprising:
   a cylinder to which channel portions are attached; and
   a piston removably fitted into the cylinder, communication states of the channel portions being switched in accordance with movement of the piston relative to the cylinder;
   wherein the cylinder comprises:
      a minimum diameter portion at which an inner diameter of the cylinder is smallest, a first channel portion of the channel portions being attached to the minimum diameter portion; and
      a blocked end portion which is provided closer to a distal end side of the cylinder in a direction of insertion of the piston into the cylinder than the minimum diameter portion of the cylinder, in an axial direction of the cylinder, and
   wherein the blocked end portion comprises:
      a minimum diameter uniform portion which is provided in one part of the blocked end portion, and which is provided flush with one part of the minimum diameter portion in the axial direction of the cylinder such that a radial distance between an inner circumferential surface of the cylinder and a longitudinal axis of the cylinder is the same at the minimum diameter portion as at the one part of the minimum diameter uniform portion, a second channel portion of the channel portions being attached to the minimum diameter uniform portion; and
      a partial diameter increased portion which is provided in the other part of the blocked end portion, and at which the inner circumferential surface of the cylinder bulges outward with respect to the minimum diameter portion in a diametrical direction of the cylinder such that the radial distance between the inner circumferential surface of the cylinder and the longitudinal axis of the cylinder is greater at the partial diameter increased portion than at the minimum diameter portion and the minimum diameter uniform portion, the partial diameter increased portion continuing to the minimum diameter uniform portion in a circumferential direction of the cylinder along the inner circumferential surface of the cylinder, the partial diameter increased portion and the minimum diameter uniform portion being open to each other along an entire length of the partial diameter increased portion in the axial direction of the cylinder, and none of the channel portions being attached to the partial diameter increased portion.

2. The endoscopic channel switching device according to claim 1, wherein a length of a chord of the minimum diameter uniform portion is the same as or longer than a diameter of the second channel portion.

3. The endoscopic channel switching device according to claim 2, wherein the inner circumferential surface of the cylinder in the minimum diameter uniform portion is in close contact with a sealing member which seals a space portion between the piston and the cylinder, and
   wherein the inner circumferential surface of the cylinder in the partial diameter increased portion is out of close contact with the sealing member so that a clearance portion as a flow portion may be formed between the inner circumferential surface and the sealing member in the diametrical direction of the cylinder.

4. The endoscopic channel switching device according to claim 1, wherein the first channel portion is attached to the minimum diameter portion at an outer circumferential surface of the cylinder.

5. The endoscopic channel switching device according to claim 1, wherein the blocked end portion has a closed end at a distal end side thereof, such that the distal end side of the cylinder is closed.

6. The endoscopic channel switching device according to claim 5, wherein no channel portions are attached to the closed end of the blocked end portion.

7. The endoscopic channel switching device according to claim 5, wherein the closed end of the blocked end portion provides a distal end of the minimum diameter uniform portion and a distal end of the partial diameter increased portion.

8. An endoscope comprising:
    an insertion portion to be inserted into a lumen;
    a channel portion which is inserted through the insertion portion; and
    the endoscopic channel switching device according to claim 1.

9. A method of manufacturing the endoscopic channel switching device according to claim 1, the method comprising:
    subjecting a thin plate to a deep-draw stepped pressing process to form, as the cylinder, a tapered cylinder having an opening portion which functions as an insertion opening portion to fit the piston into the cylinder and a bottom portion;
    forming, by bulging, the partial diameter increased portion in the blocked end portion of the cylinder;
    forming, by a pressing process, a first side surface hole in a circumferential surface of the cylinder in the minimum diameter portion;
    forming, by a pressing process, a second side surface hole portion in the circumferential surface of the cylinder in the minimum diameter uniform portion; and
    joining the first and second channel portions to the first and second side surface hole portions, respectively, and coupling the first and second channel portions to the cylinder.

10. The method according to claim 9, further comprising:
    inserting a tool into the cylinder, and finishing a coupling part between the second channel portion and the cylinder from the inside of the cylinder by the tool.

* * * * *